(12) United States Patent
Moore et al.

(10) Patent No.: US 9,241,950 B2
(45) Date of Patent: Jan. 26, 2016

(54) MIR-33 INHIBITORS AND USES THEREOF TO DECREASE INFLAMMATION

(75) Inventors: Kathryn J. Moore, Westfield, NJ (US); Katey J. Rayner, Ottowa (CA); Frederick Sheedy, New York, NY (US); Carlos Fernandez-Hernando, New York, NY (US); Yajaira Suarez, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/114,471

(22) PCT Filed: Apr. 30, 2012

(86) PCT No.: PCT/US2012/035855
§ 371 (c)(1),
(2), (4) Date: Oct. 28, 2013

(87) PCT Pub. No.: WO2012/149557
PCT Pub. Date: Nov. 1, 2012

(65) Prior Publication Data
US 2014/0080899 A1  Mar. 20, 2014

Related U.S. Application Data

(60) Provisional application No. 61/480,190, filed on Apr. 28, 2011.

(51) Int. Cl.
| | | |
|---|---|---|
| A61K 48/00 | (2006.01) | |
| C07H 21/02 | (2006.01) | |
| C07H 21/04 | (2006.01) | |
| A61K 31/713 | (2006.01) | |
| A61K 31/712 | (2006.01) | |
| C12N 15/113 | (2010.01) | |

(52) U.S. Cl.
CPC .............. *A61K 31/713* (2013.01); *A61K 31/712* (2013.01); *C12N 15/113* (2013.01); *C12N 2310/113* (2013.01); *C12N 2310/322* (2013.01); *C12N 2310/3231* (2013.01)

(58) Field of Classification Search
CPC ............................ A61K 48/00; C12N 15/113
See application file for complete search history.

(56) References Cited

U.S. PATENT DOCUMENTS

| | | | |
|---|---|---|---|
| 2006/0223777 A1 | 10/2006 | Vermeulen | |
| 2008/0300211 A1 | 12/2008 | Baltimore | |
| 2013/0245093 A1* | 9/2013 | Naar | 514/44 A |

FOREIGN PATENT DOCUMENTS

| | | | |
|---|---|---|---|
| EP | 2298359 | 3/2011 | |
| WO | 2005013901 | 2/2005 | |
| WO | 2005023986 | 3/2005 | |
| WO | 2006093526 | 9/2006 | |
| WO | 2006112872 | 10/2006 | |
| WO | 2007021896 | 2/2007 | |
| WO | 2007027775 | 3/2007 | |
| WO | 2007027894 | 3/2007 | |
| WO | 2007090073 | 8/2007 | |
| WO | 2007112753 | 10/2007 | |
| WO | 2007112754 | 10/2007 | |
| WO | 2008046911 | 4/2008 | |
| WO | 2008074328 | 6/2008 | |
| WO | 2008091703 | 7/2008 | |
| WO | 2008142567 | 11/2008 | |
| WO | 2009020771 | 2/2009 | |
| WO | WO2009043353 A2 * | 4/2009 | 514/44 |
| WO | 2010120508 | 10/2010 | |
| WO | 2012027601 | 3/2012 | |
| WO | 2012027704 | 3/2012 | |

OTHER PUBLICATIONS

Couture, et al., "Anti-gene therapy: the use of ribozymes to inhibit gene function", Trends Genet., 12:510-5 (1996).
Davis, et al., "Potent inhibition of microRNA in vivo without degradation", Nucleic Acids Res 37:70-77 (2009).
Elmen, et al., "LNA-mediated microRNA silencing in non-human primates", Nature, 452:896-9 (2008).
Gumireddy, et al., Small-molecule inhibitors of microma miR-21 function. Angew Chem Int Ed Engl., 47(39);7482-4 (2008).
Henry, et al., "Chemically modified oligonucleotides exhibit decreased immune stimulation in mice", J Pharmacol Exp Ther., 292:468-79 (2000).
Lanford, et al., "Therapeutic silencing of microRNA-122 in primates with chronic hepatitis C virus infection", Science, 327:198-201 (2010).
Paszty, et al., "Apolipoprotein AI transgene corrects apolipoprotein E deficiency-induced atherosclerosis in mice", J Clin Invest., 94:899-903 (1994).
Plump, et al., "Human apolipoprotein A-I gene expression increases high density lipoprotein and suppresses atherosclerosis in the apolipoprotein E-deficient mouse", PNAS, 91:9607-11(1994).
Rayner, et al., "Antagonism of miR-33 in mice promotes reverse cholesterol transport and regression of atherosclerosis", J Clin. Inv., 121(7):2921-31 (2011).
Rong, et al., "Elevating high-density lipoprotein cholesterol in apolipoprotein E-deficient mice remodels advanced atherosclerotic lesions by decreasing macrophage and increasing smooth muscle cell content", Circulation, 104:2447-52 (2001).
Rubin, et al., "Inhibition of early atherogenesis in transgenic mice by human apolipoprotein AI", Nature, 353:265-7 (1991).
Wang, et al., "Macrophage ABCA1 and ABCG1, but not SR-BI, promote macrophage reverse cholesterol transport in vivo", J. Clin. Invest., 117:2216-24 (2007).
Zhang, et al., "Hepatic expression of scavenger receptor class B type I (SR-BI) is a positive regulator of macrophage reverse cholesterol transport in vivo", J. Clin. Invest. 115:2870-4 (2005).

\* cited by examiner

*Primary Examiner* — Amy Bowman
(74) *Attorney, Agent, or Firm* — Pabst Patent Group LLP

(57) ABSTRACT

The inhibition of miRNA miR-33 is shown to promote the polarization of macrophages from an M1 to an M2 phenotype. MiR-33 inhibitors are therefore useful for treating inflammation in subjects. Endogenous microRNAs can be silenced using antagomirs. The miR-33 inhibitor is preferably an antagomir having a single-stranded nucleic acid sequence that is complementary to at least 12 contiguous nucleotides in miR-33 and therefore forms a duplex with miR-33 under physiological conditions.

18 Claims, 18 Drawing Sheets

SEQUENCE LISTING

```
<160> NUMBER OF SEQ ID NOS: 4

<210> SEQ ID NO 1
<211> LENGTH: 22
<212> TYPE: RNA
<213> ORGANISM: Homo sapiens

<400> SEQUENCE: 1
caauguuucc acagugcauc ac                                            22

<210> SEQ ID NO 2
<211> LENGTH: 21
<212> TYPE: RNA
<213> ORGANISM: Homo sapiens

<400> SEQUENCE: 2
gugcauugua guugcauugc a                                             21

<210> SEQ ID NO 3
<211> LENGTH: 20
<212> TYPE: RNA
<213> ORGANISM: Homo sapiens

<400> SEQUENCE: 3
gugcauugcu guugcauugc                                               20

<210> SEQ ID NO 4
<211> LENGTH: 22
<212> TYPE: RNA
<213> ORGANISM: Homo sapiens

<400> SEQUENCE: 4
cagugccucg gcagugcagc cc                                            22
```

MIR-33 INHIBITORS AND USES THEREOF TO DECREASE INFLAMMATION

This application is a 371 application of the International Application No. PCT/US2012/035855 entitled "miR-33 Inhibitors and Uses Thereof to Decrease Inflammation", filed in the United States Receiving Office for the PCT on Apr. 30, 2012, which claims the benefit of and priority to U.S. Provisional Application No. 61/480,190 filed Apr. 28, 2011, which is hereby incorporated herein by reference in its entirety.

STATEMENT REGARDING FEDERALLY SPONSORED RESEARCH OR DEVELOPMENT

This invention was made with government support under Grant Nos. R01AG02055. R01HL084312, P01HL098055 and R00 HL088528 awarded by the National Institutes of Health. The Government has certain rights in the invention.

REFERENCE TO SEQUENCE LISTING

The Sequence Listing submitted Oct. 28, 2013 as a text file named "NYUMC_MOO_02_01_ST25.txt," created on Oct. 28, 2013, and having a size of 1,003 bytes is hereby incorporated by reference pursuant to 37 C.F.R. §1.52(e)(5).

FIELD OF THE INVENTION

The invention is generally related to the field of molecular biology, more specifically to the field of antagomirs and their use in inhibiting microRNAs for inhibiting inflammation and treating inflammatory disease.

BACKGROUND OF THE INVENTION

The immune system is required for defending the host against infections. However, immune responses are themselves capable of causing tissue injury and disease. Injurious, or pathologic, immune reactions are called hypersensitivity reactions. This term is derived from the idea that an immune response to an antigen may result in sensitivity to challenge with that antigen and, therefore, hypersensitivity is a reflection of excessive or aberrant immune responses. Hypersensitivity reactions may occur in two situations. First, responses to foreign antigens may be dysregulated or uncontrolled, resulting in tissue injury. Second, the immune responses may be directed against self (autologous) antigens, as a result of the failure of self-tolerance. Responses against self antigens are termed autoimmunity, and disorders caused by such responses are called autoimmune diseases.

Much of the damage resulting from inflammation is due to a shift in the polarization of macrophage M1 and M2 phenotypes. M1 macrophages produce copious amounts of reactive oxygen and nitrogen intermediates and inflammatory cytokines; are part of the afferent and efferent limb of polarized Th1 responses; and mediate resistance against intracellular parasites and tumors. M2 cells are generally involved in the T helper 2 (Th2) response; have immunoregulatory function; orchestrate encapsulation and containment of parasites; and promote tissue repair, remodeling, and tumor progression. Therefore, whereas M1 macrophages are generally destructive, M2 macrophages are generally reparative.

It is therefore an object of the invention to provide therapeutic compositions and methods for reducing inflammation in a tissue of a subject.

It is another object of the invention to provide compositions and methods for shifting the polarization of macrophages from an M1 phenotype to an M2 phenotype.

It is a further object of the invention to provide therapeutic compositions and methods for treating inflammatory diseases.

SUMMARY OF THE INVENTION

Compositions and methods for inhibiting inflammation in a tissue have been discovered. In particular, the compositions and methods relate to the ability of miR-33 inhibitors to modulate the polarization of macrophages from a pro-inflammatory M1 state to a reparative M2 state.

The destructive and reparative stages of a macrophage have been divided into M1 and M2 macrophage subtypes respectively. M1 macrophages typically take part in the initial immune response to invading microorganisms and promote T helper (Th) 1 immunity, whereas M2 macrophages are induced during the resolution phase of inflammation and are involved in debris scavenging, tissue remodeling, and promotion of Th2 immunity. Polarization of macrophages is directed by the microenvironment. M1 macrophages are induced by interferon-γ and microbial products such as lipopolysaccharide. On the other hand, M2 macrophages are induced by Th2- or anti-inflammatory cytokines and growth factors, including IL-4, IL-10 and transforming growth factor-β.

In some embodiments, one or more anti-inflammatory cytokine genes that promote M2 inflammatory response have binding sites for miR-33 in their 3'UTR, such that miR-33 binding represses gene expression. In some of these embodiments, inhibitors of miR-33 derepress the M2 cytokine genes and thereby promote M2 macrophages.

Methods of reducing inflammation in a tissue of a subject are disclosed that involve administering to the subject a therapeutically effective amount of an miR-33 inhibitor. In preferred embodiments, the subject has inflammation in one or more tissues characterized by M1 macrophage phenotype, Th1 immunity, or combinations thereof. In some embodiments, the inflammation is acute. In other embodiments, the inflammation is chronic.

In some embodiments, the subject has an inflammatory disease. For example, the inflammatory disease can be the result of harmful stimuli, such as pathogens, damaged cells, or irritants. The inflammatory disease can also be the result of hypersensitivity or autoimmunity.

The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. Examples of disorders associated with inflammation include: acne vulgaris, asthma, atherosclerosis, autoimmune diseases, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, and interstitial cystitis.

Atherosclerosis involves an ongoing inflammatory response. Inflammation is involved in mediating all stages of atherosclerosis from initiation through progression and, ultimately, the thrombotic complications of atherosclerosis. Inhibitors of miR-33 have been shown to increase serum HDL levels and decrease serum triglycerides. Therefore, miR-33 inhibitors are effective for treating atherosclerosis on two fronts, i.e., reducing fatty materials (lipids and cholesterols) and decreasing inflammation. However, in some embodiments of the disclosed compositions and methods, the inflammatory disease is not atherosclerosis and the inflammation does not occur within an atherosclerotic plaque.

A therapeutically effective amount of an miR-33 inhibitor in a pharmaceutically acceptable carrier can be administered to an individual in need thereof. Endogenous microRNAs can be silenced using antagomirs, which are small RNA that are complementary to the microRNAs target. The miR-33 inhibitor is preferably an antagomir having a single-stranded nucleic acid sequence that is complementary to at least 12 contiguous nucleotides in miR-33, wherein the antisense oligonucleotide forms a duplex with miR-33 under physiological conditions.

In preferred embodiments, the miR-33 inhibitor is a single stranded nucleic acid sequence that hybridizes under stringent conditions to an oligonucleotide consisting of the nucleic acid sequence SEQ ID NO:1, SEQ ID NO:2, or SEQ ID NO:3.

Antagomirs are preferably modified to make them more resistant to degradation. The antisense oligonucleotide preferably comprises one or more nucleotide modifications that increase stability of the antisense oligonucleotide in the presence of a nuclease. For example, in some embodiments, one or more of the nucleotide units of the antisense oligonucleotide are locked nucleic acid (LNA) units. In some embodiments, one or more of the nucleotide units of the antisense oligonucleotide are 2' substituted nucleotide analogues. For example, one or more of the internucleoside linkages between the nucleotide units of the antisense oligonucleotide can be phosphorothioate internucleoside linkages.

DETAILED DESCRIPTION OF THE INVENTION

I. Definitions

Figure 1A:
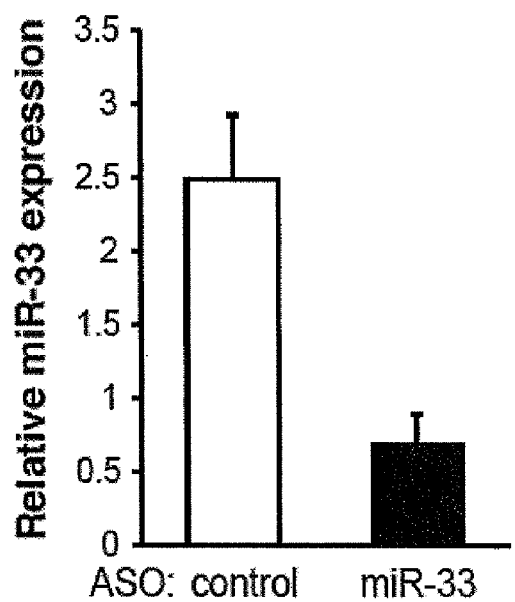
FIG. 1A is a bar graph showing relative miR-33 expression in livers of anti-miR33 treated mice (solid bar) compared to mice treated with control anti-miR (open bar).

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience., 1999; and Robert A. Meyers (ed.), Molecular Biology and Biotechnology, a Comprehensive Desk Reference, published by VCH Publishers, Inc., 1995; Sambrook and Russell. (2001) Molecular Cloning: A Laboratory Manual 3rd. edition, Cold Spring Harbor Laboratory Press.

To facilitate understanding of the disclosure, the following definitions are provided:

The term "inflammation" refers to complex reaction of the innate immune system in vascularized tissues that involves the accumulation and activation of leukocytes and plasma proteins at a site of infection, toxin exposure, or cell injury. Inflammation is initiated by changes in blood vessels that promote leukocyte recruitment. Local adaptive immune responses can promote inflammation. Although inflammation serves a protective function in controlling infections and promoting tissue repair, it can also cause tissue damage and disease.

The term "macrophage" refers to a tissue-based phagocytic cell, derived from blood monocytes, that plays important roles in innate and adaptive immune responses. Macrophages are activated by microbial products, such as endotoxin, by molecules such as CD40 ligand, and by T cell cytokines such as interferon-γ. Activated macrophages phagocytose and kill microorganisms, secrete proinflammatory cytokines, and present antigens to helper T cells. Macrophages may assume different morphologic forms in different tissues, including the microglial cells of the central nervous system, Kupffer cells in the liver, alveolar macrophages in the lung, and osteoclasts in bone.

An "isolated" nucleic acid molecule or polynucleotide is a nucleic acid molecule that is identified and separated from at least one substance with which it is ordinarily associated in the natural source. The isolated nucleic can be, for example, free of association with all components with which it is naturally associated. An isolated nucleic acid molecule is other than in the form or setting in which it is found in nature.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

The term "promoter" refers to a regulatory nucleic acid sequence, typically located upstream (5') of a gene or protein coding sequence that, in conjunction with various elements, is responsible for regulating the expression of the gene or protein coding sequence.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "endogenous" with regard to a nucleic acid refers to nucleic acids normally present in the host.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "nucleic acid" may be used to refer to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

The term "oligonucleotide" refers to a single-stranded nucleic acid polymer of a defined sequence that can base-pair to a second single-stranded nucleic acid polymer that contains a complementary sequence.

The term "oligoribonucleotide" refers to an oligonucleotide containing ribonucleotides.

The term "nucleotide" refers to one or more monomeric subunits of an oligonucleotide agent. The term "nucleotide" can also generally refer to a modified nucleotide or surrogate replacement moiety.

The term "ribonucleotide" is a nucleotide in which a purine or pyrimidine base is linked to a ribose molecule.

The term "duplex" or "double-stranded" refers to the linkage of two nucleic acid polymers by complementary base pairing.

The term "complementary" and "complementarity" refers to the rules of Watson and Crick base pairing. For example, A (adenine) bonds with T (thymine) or U (uracil), G (guanine) bonds with C (cytosine). For example, DNA contains an antisense strand that is complementary to its sense strand. A nucleic acid that is 95% identical to a DNA antisense strand is therefore 95% complementary to the DNA sense strand.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1× SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

The term "treat" or "treatment" as used herein means the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" as used herein does not require absolute forestalling of the condition or disease but can also include a reduction in the onset or severity of the disease or condition. Thus, if a therapy can treat a disease in a subject having symptoms of the disease, it can also prevent that disease in a subject who has yet to suffer some or all of the symptoms.

The term "therapeutically effective" means that the amount of the composition used is of sufficient quantity to ameliorate one or more causes or symptoms of a disease or disorder. Such amelioration only requires a reduction or alteration, not necessarily elimination.

II. miRNA inhibitors

The miRNA miR-33 is shown herein to be pro-inflammatory mediators of an M1 macrophage phenotype. Inhibitors of miR-33 are shown to promote the polarization of macrophages from an M1 to an M2 phenotype and reduce inflammation. Specifically, miR-33 antagomirs can reduce expression of M1 markers of inflammation (IL-1 and TNFα) in macrophages while increasing expression of M2 markers (Arg1, IL-10, IL-4, and Fizz1). Notably, both Arg1 and IL-10 contain a single miR-33 binding site in their 3'UTRs and as such, the increase in Arg1 and IL-10 mRNA in macrophages of anti-miR-33 treated mice and macrophages in vitro may represent derepression of these target genes.

Therefore miR-33 inhibitors are provided for use in reducing inflammation and treating inflammatory diseases. Useful miR-33 inhibitors can be obtained by screening libraries of known compounds, including compounds of unknown function, to see if they inhibit miR-33, as described in the examples. Preferred inhibitors are compounds which are orally bioavailable, and exhibit low toxicity.

A. Antagomirs

In some embodiments, the miR-33 inhibitor is an antagomir. An "antagomir" refers to a single stranded, double stranded, partially double stranded or hairpin structured oligomer or polymer of ribonucleic acid (RNA) or deoxyribonucleic acid (DNA) or both or modifications thereof, which is antisense with respect to its miRNA target.

Examples of antagomirs and other miRNA inhibitors are described in WO2009/20771, WO2008/91703, WO2008/046911, WO2008/074328, WO2007/90073, WO2007/27775, WO2007/27894, WO2007/21896, WO2006/93526, WO2006/112872, WO2007/112753, WO2007/112754, WO2005/23986, or WO2005/13901, all of which are hereby incorporated by reference.

Custom designed Anti-miR™ molecules are commercially available from Applied Biosystems. Thus, in some embodiments, the antagomir is an Ambion® Anti-miR™ inhibitor. These molecules are chemically modified and optimized single-stranded nucleic acids designed to specifically inhibit naturally occurring mature miRNA molecules in cells. For example, product ID AM12607 from Applied Biosystems is an Ambion® Anti-miR™ inhibitor targeting human miR-33a.

Custom designed Dharmacon Meridian™ microRNA Hairpin Inhibitors are also commercially available from Thermo Scientific. These inhibitors include chemical modifications and secondary structure motifs. For example, Vermeulen et al. reports in U.S. Patent Publication 2006/0223777 the identification of secondary structural elements that enhance the potency of these molecules. Specifically, incorporation of highly structured, double-stranded flanking regions around the reverse complement core significantly increases inhibitor function and allows for multi-miRNA inhibition at subnanomolar concentrations. Other such improvements in antagomir design are contemplated for use in the disclosed methods.

In preferred embodiments, the disclosed antagomir includes a region of sufficient nucleotide length and sufficient complementarity to miR-33 that the antagomir forms a duplex with miR-33. Given the sequence of miR-33, an antagomir can be designed according to the rules of Watson and Crick base pairing.

Thus, the antagomir can be an antisense oligonucleotide having a single-stranded nucleic acid sequence that is complementary to at least 8, 9, 10, 11, 12, 13, 14, 15, 16, 17, 18, 19, 20, 21, 22, 23, or 24 contiguous nucleotides in miR-33, wherein the antisense oligonucleotide forms a duplex with miR-33 under physiological conditions.

The following is a schematic of human miR-33a stem loop:

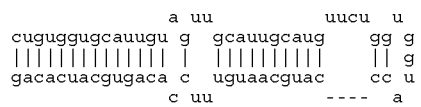

In certain embodiments, human miR-33a can have the nucleic acid sequence GUGCAUUGUAGUUGCAUUGCA (SEQ ID NO:2). Thus, in certain embodiments, the single-stranded nucleic acid sequence hybridizes under stringent conditions to an oligonucleotide having the sequence of SEQ ID NO:2. In certain embodiments, human miR-33a* can have the nucleic acid sequence: CAAUGUUUCCACAGUGCAU-CAC (SEQ ID NO:1). Therefore, in certain embodiments, the single-stranded nucleic acid sequence hybridizes under stringent conditions to an oligonucleotide having the of nucleic acid sequence SEQ ID NO:1.

The following is a schematic of human miR-33b stem loop:

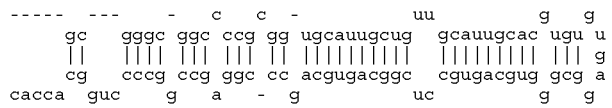

In certain embodiments, human miR-33b can have the nucleic acid sequence of GUGCAUUGCUGUUGCAUUGC (SEQ ID NO:3). Thus, in certain embodiments, the single-stranded nucleic acid sequence hybridizes under stringent conditions to an oligonucleotide having the sequence of SEQ ID NO:3. In certain embodiments, human miR-33b* can have the nucleic acid sequence CAGUGCCUCGGCAGUG-CAGCCC (SEQ ID NO:4). Therefore, in certain embodiments, the single-stranded nucleic acid sequence hybridizes under stringent conditions to an oligonucleotide having the of nucleic acid sequence SEQ ID NO:4.

In some embodiments, a single-stranded nucleic acid sequence hybridizes under stringent conditions to an oligonucleotide having the sequence of SEQ ID NO:2, and hybridizes under stringent conditions to an oligonucleotide having the sequence of SEQ ID NO:3.

In some embodiments, miR-33 ismiR-33a. In some embodiments, miR-33 is miR-33b.

In preferred embodiments, the antisense oligonucleotide contains one or more nucleotide modifications that increase stability of the antisense oligonucleotide in the presence of a nuclease. For example, one or more of the nucleotide units of the antisense oligonucleotide can be locked nucleic acid (LNA) units. In some embodiments, one or more of the nucleotide units of the antisense oligonucleotide are 2' substituted nucleotide analogues. Additionally, one or more of the internucleoside linkages between the nucleotide units of the antisense oligonucleotide can be phosphorothioate internucleoside linkages. It is understood that the antisense oligonucleotide can include one or more different types of modifications. Thus, the antisense oligonucleotide can have LNA units, 2' substituted nucleotide analogues, and phosphorothioate internucleoside linkages. Other modifications that are suitable for improving therapeutic use of a nucleic acid, such as an RNA molecule, can also be used with the disclosed antisense oligonucleotide.

1. Length

The antagomir can include an antisense oligonucleotide having a length of at least 8 contiguous nucleotides. Therefore, the antisense oligonucleotide can have 8, 9, 10, 11, 12, 13, 14, 15, 16, 17, 18, 19, 20, 21, 22, 23, or 24 contiguous nucleotides. The oligonucleotide is preferably less than 30 contiguous nucleotides in length. The oligonucleotide can be less than 25, 26, 27, 28, 29, 30, 31, 32, 33, 34, 35, 36, 37, 38, 39, 40 contiguous nucleotides in length 2. Complementarity The disclosed antagomir can include an antisense oligonucleotide having a region that is at least partially, and in some embodiments fully, complementary to miR-33. It is not necessary that there be perfect complementarity between the antagomir and the target, but the correspondence must be sufficient to enable the antisense oligonucleotide to duplex with miR-33 and subsequently reduce its activity. For example, in preferred embodiments, the antisense oligonucleotide inhibits miR-33 binding to the 3'UTR of ABCA1.

The disclosed antagomir can include an antisense oligonucleotide having a region that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementary to miR-33.

Preferably, the disclosed antagomir has at least 6, 7, 8, 9, 10, 11, 12, 13, 14, 15, 16, 17, 18, 19, 20 or more contiguous nucleotides complementary to an miR-33 nucleotide sequence. In one embodiment, the disclosed antagomir has a nucleotide sequence that is complementary to miR-33. Thus, in one embodiment, the disclosed antagomir has at least 6, 7, 8, 9, 10, 11, 12, 13, 14, 15, 16, 17, 18, 19, 20 or more contiguous nucleotides that are complementary to miR-33.

In some embodiments, there will be nucleotide mismatches in the region of complementarity. In a preferred embodiment, the region of complementarity will have no more than 1, 2, 3, 4, or 5 mismatches.

In some embodiments, the antagomir is "exactly complementary" to miR-33. Thus, in one embodiment, the antagomir can anneal to miR-33 to form a hybrid made exclusively of Watson-Crick base pairs in the region of exact complementarity. Thus, in some embodiments, the antagomir specifically discriminates a single-nucleotide difference. In this case, the antagomir only inhibits miR-33 activity if exact complementarity is found in the region of the single-nucleotide difference.

3. Modifications

The disclosed antagomirs include oligomers or polymers of ribonucleic acid (RNA) or deoxyribonucleic acid (DNA) or both or modifications thereof. This term includes oligonucleotides composed of naturally occurring nucleobases, sugars, and covalent internucleoside (backbone) linkages as well as oligonucleotides having non-naturally-occurring portions that similarly. Such modified or substituted oligonucleotides are often preferred over native forms because of desirable properties such as, for example, enhanced cellular uptake, enhanced affinity for nucleic acid target, and/or increased stability in the presence of nucleases.

The antagomir oligonucleotide can include unmodified RNA and DNA as well as RNA and DNA that have been modified, e.g., to improve efficacy, and polymers of nucleoside surrogates. "Unmodified" RNA refers to a molecule in which the components of the nucleic acid, namely sugars, bases, and phosphate moieties, are the same or essentially the same as that which occur in nature, preferably as occur naturally in the human body. "Modified" RNA, as used herein, refers to a molecule where one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs.

The disclosed antagomir oligonucleotide can be modified to enhance resistance to nucleases. The antagomir oligonucleotide can include nucleotide modification that stabilized it against nucleolytic degradation. The oligomer can be a totalmer, mixmer, gapmer, tailmer, headmer or blockmer. A "totalmer" is a single stranded oligonucleotide that only comprises non-naturally occurring nucleotides.

The term "gapmer" refers to an oligonucleotide composed of modified nucleic acid segments flanking at least 5 naturally occurring nucleotides (i.e., unmodified nucleic acids).

The term "blockmer" refers to a central modified nucleic acid segment flanked by nucleic acid segments of at least 5 naturally occurring nucleotides.

The term "tailmer" refers to an oligonucleotide having at least 5 naturally occurring nucleotides at the 5'-end followed by a modified nucleic acid segment at the 3'-end.

The term "headmer" refers to oligonucleotide having a modified nucleic acid segment at the 5'-end followed by at least 5 naturally occurring nucleotides at the 3'-end.

The term "mixmer" refers to oligonucleotide which comprise both naturally and non-naturally occurring nucleotides. However, unlike gapmers, tailmers, headmers and blockmers, there is no contiguous sequence of more than 5 naturally occurring nucleotides, such as DNA units.

Modified nucleic acids and nucleotide surrogates can include one or more of (i) replacement of one or both of the non-linking phosphate oxygens and/or of one or more of the linking phosphate oxygens; (ii) replacement of a constituent of the ribose sugar, e.g., of the 2' hydroxyl on the ribose sugar, or wholesale replacement of the ribose sugar with a structure other than ribose; (iii) wholesale replacement of the phosphate moiety with "dephospho" linkers; (iv) modification or replacement of a naturally occurring base; (v) replacement or modification of the ribose-phosphate backbone; or (vi) modification of the 3' end or 5' end of the RNA, e.g., removal, modification or replacement of a terminal phosphate group or conjugation of a moiety, such as a fluorescently labeled moiety, to either the 3' or 5' end of RNA.

The phosphate group in a nucleic acid can be modified by replacing one of the oxygen atoms with a different substituent. One result of this modification to RNA phosphate backbones can be increased resistance of the oligoribonucleotide to nucleolytic breakdown. Thus, it can be desirable in some embodiments to introduce alterations that result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur.

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen.

The phosphate group can be replaced by non-phosphorus containing connectors. Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

A modified RNA can include modification of all or some of the sugar groups of the ribonucleic acid. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; amine, O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). Oligonucleotides containing only the methoxyethyl group (MOE) ($OCH_2CH_2OCH_3$, a PEG derivative) exhibit nuclease stabilities comparable to those modified with the robust phosphorothioate modification.

"Deoxy" modifications include hydrogen (i.e., deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O) R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Thus, the antagomir can include a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). in some embodiments, the antagomir includes at least one 2'-O-methyl-modified nucleotide, and in some embodiments, all of the nucleotides of the antagomir include a 2'-O-methyl modification.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also further contain modifications at one or more of the constituent sugar atoms. The modification can also entail the wholesale replacement of a ribose structure with another entity (an SRMS) at one or more sites in the oligonucleotide agent.

The 3' and 5' ends of an oligonucleotide can be modified. Such modifications can be at the 3' end, 5' end, or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' 0, N, S or C group of the sugar. Alternatively, the spacer can connect to or replace the terminal atom of a nucleotide surrogate (e.g., PNAs). These spacers or linkers can include e.g., $—(CH_2)_n—$, $—(CH_2)_nN—$, $—(CH_2)_nO—$, $—(CH_2)_nS—$, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents.

Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. For example, in some embodiments, oligonucleotide agents are 5' phosphorylated or include a phosphoryl analog at the 5' terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl-methyl, ethyl, isopropyl, propyl, etc., e.g. RP(OH)(O)—O-5'-, (OH)$_2$(O)P-5'-CH$_2$—), 5'-alkyletherphosphonates (R=alkylether=methoxymethyl (MeOCH$_2$—), ethoxymethyl, etc., e.g. RP(OH)(O)—O-5'-).

Adenine, guanine, cytosine and uracil are the most common bases found in RNA. These bases can be modified or replaced to provide RNAs having improved properties. For example, nuclease resistant oligonucleotides (i.e., oligoribonucleotides) can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases", can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynyleytosine, dihydrouracil, 3-deaza-5-azacytosine, 2-aminopurine, 5-alkyluracil, 7-alkylguanine, 5-alkyl cytosine,7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N.sup.4-acetyl cytosine, 2-thiocytosine, N6-methyladenine, N6-isopentyladenine, 2-methylthio-N6-isopentenyladenine, N-methylguanines, or O-alkylated bases.

The antagomir can include an internucleotide linkage (e.g., the chiral phosphorothioate linkage) useful for increasing nuclease resistance.

Phosphorothioates (or S-oligos) are a variant of normal DNA or RNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, plasma nucleases and snake venom phosphodiesterase. In addition, the potential for crossing the lipid bilayer increases. Because of these important improvements, phosphorothioates have found increasing application in cell regulation.

Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1,1-dioxide (BDTD).

One way to increase resistance is to identify cleavage sites and modify such sites to inhibit cleavage. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. Thus, the antagomir can include at least 2, 3, 4 or 5 of such dinucleotides. In certain embodiments, all the pyrimidines of an antagomir carry a 2'-modification, and the antagomir therefore has enhanced resistance to endonucleases.

An antagomir can have secondary structure, but it is preferably substantially single-stranded under physiological conditions at least in the region of the antagomir that is complementary to the miRNA. An antagomir that is substantially single-stranded is single-stranded to the extent that less than about 50% (e.g., less than about 40%, 30%, 20%, 10%, or 5%) of the antagomir is duplexed with itself. Thus, the antagomir preferably does not form hairpin loops, bulges or internal loops within the complementary region under physiological conditions.

In a preferred embodiment, the antagomir does not include a sense strand. In some embodiments, the antagomir is partially double-stranded but is single-stranded at least in the region of the antagomir that is complementary to the miRNA. The term "partially double-stranded" refers to double stranded structures wherein one strand contains fewer nucleotides than its complementary strand. In general, such partial double stranded agents will have less than 75% double stranded structure, preferably less than 50%, and more preferably less than 25%, 20% or 15% double stranded structure.

In a preferred embodiment, the antagomir is suitable for delivery to a cell in vivo, e.g., to a cell in an organism. In another embodiment, the antagomir is suitable for delivery to a cell in vitro, e.g., to a cell in a cell line in culture or a suspension. The antagomir can include a ligand that is selected to improve stability, distribution or cellular uptake of the agent. For example, the ligand can be a lipophilic moiety, e.g., cholesterol, which enhances entry of the antagomir into a cell.

The antagomir can also be encapsulated by cationic lipid particles. Cationic lipid saturation influences intracellular delivery of encapsulated nucleic acids. Cationic lipids include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA) and 1,2-dilinolenyloxy-N,N-dimethyl-3-aminopropane (DLenDMA).

In some embodiments, the disclosed antagomir can include an aminoglycoside ligand, which can cause the antagomir to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

The disclosed antagomir can be expressed within cells from an expression vector having a nucleic acid encoding the antagomir. The nucleic acid sequence can be operably linked to an expression control sequence, such as a promoter. Those skilled in the art realize that any nucleic acid can be expressed in eukaryotic cells from the appropriate DNA/RNA vector.

Thus, the disclosed antagomir can be expressed from transcription units inserted into DNA or RNA vectors. The recombinant vectors can be DNA plasmids or viral vectors. Oligonucleotide agent-expressing viral vectors can be constructed based on, but not limited to, adeno-associated virus, retrovirus, lentivirus, adenovirus, or alphavirus. The recombinant vectors capable of expressing the oligonucleotide agents can be delivered as described above, and can persist in target cells. Alternatively, viral vectors can be used that provide for transient expression of nucleic acid molecules. Such vectors can be repeatedly administered as necessary. Once expressed, the disclosed antagomir interacts with miR-333 and inhibits its activity. In preferred embodiments, the at least part of the antagomir forms a duplex with endogenous miR-33, which prevents the endogenous miR-33 from binding to its target mRNA (e.g., ABCA1), which results in increased translation of the target mRNA. Delivery of oligonucleotide agent-expressing vectors can be systemic, such as by intravenous or intra-muscular administration, by administration to target cells ex-planted from a subject followed by reintroduction into the subject, or by any other means that would allow for introduction into the desired target cell (for a review see Couture et al., Trends in Genetics 12:510, 1996).

B. Small Molecule miR-33 Inhibitors

The miR-33 inhibitor can also be a small molecule inhibitor. As used herein, the term "small molecule" refers to small organic compounds, inorganic compounds, or any combination thereof that inhibits or reduces miR-33 activity; this term may include monomers or primary metabolites, secondary metabolites, a biological amine, a steroid, or synthetic or natural, non-peptide biological molecule(s).

For example, Huang and his colleagues developed a method to identify inhibitors of miRNA pathways in live human cells (Angew Chem Int Ed Engl. 2008; 47(39):7482-4). Specifically, they designed a screening assay to look for small molecules or compounds that selectively repress miRNA. They selected miR-21 as the target agent due to its documented role in preventing cell death—thereby allowing the unchecked cell proliferation associated with cancer—and its elevated levels in various cancers. Their assay contained the DNA binding sequence complementary to the miRNA, bound to a reporter such as luciferase. Under normal conditions, the miRNA binds to the complementary sequence and inhibits the translation of the reporter, such as luciferase. Candidate agents were then be added to the sample to determine whether the candidate agent reduced miRNA inhibition of reporter expression.

Thus, a method is provided that involves providing a sample having an oligonucleotide with a DNA binding sequence complementary to miR-33 under conditions that allow the binding of miR-33 to the oligonucleotide, contacting the sample with a candidate agent, detecting the level of miR-33/oligonucleotide binding, comparing the binding level to a control, a decrease in miR-33/oligonucleotide binding compared to the control identifying an miR-33 inhibitor.

The binding of miR-33 to the oligonucleotide can be detected using routine methods. In a preferred aspect, the DNA binding sequence complementary to miR-33 is operably linked to a reporter construct, such as luciferase or GFP, wherein binding of miR-33 to the oligonucleotide inhibits reporter expression.

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits miRNA. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

III. Methods of Making Antagomirs and Formulations Thereof

An antagomir, such as a single-stranded oligonucleotide agent, can be constructed using chemical synthesis and/or enzymatic ligation reactions using procedures known in the art. For example, an antagomir can be chemically synthesized using naturally occurring nucleotides or variously modified nucleotides designed to increase the biological stability of the molecules or to increase the physical stability of the duplex formed between the antagomir and target nucleic acids, e.g., phosphorothioate derivatives and acridine substituted nucleotides can be used. Other appropriate nucleic acid modifications are described herein. Alternatively, the antagomir can be produced biologically using an expression vector into which a nucleic acid has been subcloned in an antisense orientation (i.e., RNA transcribed from the inserted nucleic acid will be of an antisense orientation to a target nucleic acid of interest (e.g., miR-33).

A. Formulation

The miR-33 inhibitor composition can be formulated for administration to a subject. Methods for preparing pharmaceutical compositions are within the skill in the art, for example as described in Remington's Pharmaceutical Science, 18th ed., Mack Publishing Company, Easton, Pa. (1990), and The Science and Practice of Pharmacy, 2003, Gennaro et al.

In one embodiment, the formulations include antagomir (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, or 0.3% glycine, for injection.

The pharmaceutical formulations can also include conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (e.g., calcium DTPA, CaNaDTPA-bisamide), or, optionally, additions of calcium or sodium salts (for example, calcium chloride, calcium ascorbate, calcium gluconate or calcium lactate). Pharmaceutical compositions can be packaged for use in liquid form, or can be lyophilized.

For solid compositions, conventional non-toxic solid carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can include any of the carriers and excipients listed above and 10-95%, preferably 25%-75%, of one or more single-stranded oligonucleotide agents.

A formulated compound may assume a variety of states. In some examples, the composition is at least partially crystalline, uniformly crystalline, and/or anhydrous (e.g., less than 80, 50, 30, 20, or 10% water). In another example, the antagomir is in an aqueous phase, e.g., in a solution that includes water, this form being the preferred form for administration via inhalation.

The compound can be incorporated into a delivery vehicle, e.g., a liposome (particularly for the aqueous phase), or a particle (e.g., a microparticle). Generally, the compound is formulated in a manner that is compatible with the intended method of administration.

The MiR-33 inhibitor composition formulations can include liposomes, such as surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug.

Long-circulating liposomes enhance the pharmacokinetics and pharmacodynamics of DNA and RNA, particularly compared to conventional cationic liposomes which are known to accumulate in tissues of the MPS. Long-circulating liposomes are also likely to protect drugs from nuclease degradation to a greater extent compared to cationic liposomes, based on their ability to avoid accumulation in metabolically aggressive MPS tissues such as the liver and spleen.

The types of pharmaceutical excipients that are useful as carrier include stabilizers such as human plasma albumin (HSA), bulking agents such as carbohydrates, amino acids and polypeptides; pH adjusters or buffers; salts such as sodium chloride; and the like. These carriers may be in a crystalline or amorphous form or may be a mixture of the two. Bulking agents that are particularly valuable include compatible carbohydrates, polypeptides, amino acids or combinations thereof. Suitable carbohydrates include monosaccharides such as galactose, D-mannose, and sorbose; disaccharides, such as lactose and trehalose; cyclodextrins, such as 2-hydroxypropyl.beta.-cyclodextrin; and polysaccharides, such as raffinose, maltodextrins, and dextrans; alditols, such as mannitol and xylitol. A preferred group of carbohydrates includes lactose, threhalose, raffinose maltodextrins, and mannitol. Suitable polypeptides include aspartame. Amino acids include alanine and glycine, with glycine being preferred.

B. Combinations

A compound can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as $Mg^{2+}$), salts, and RNAse inhibitors (e.g., a broad specificity RNAse inhibitor such as RNAsin).

In one embodiment, the antagomir preparation includes another antagomir, e.g., a second antagomir that can down-regulate expression of a second miRNA. In some embodiments, the agents are directed to the same target nucleic acid but different target sequences. In another embodiment, each antagomir is directed to a different target.

A compound can be formulated in combination with one or more other compounds, especially other compounds involved in inhibition of cholesterol synthesis or uptake, such as a statin, bile acid sequestrants, cholesterol absorption inhibitors such as fibrate, nicotinic acid, etc.

IV. Methods of Administration and Disorders to be Treated

A. Methods of Administration

A miR-33 inhibitor may be administered in a number of ways depending upon whether local or systemic treatment is desired and upon the area to be treated. Administration may be topical (including ophthalmic, intranasal, transdermal, intrapulmonary), oral or parenteral. Parenteral administration includes intravenous drip, subcutaneous, intraperitoneal or intramuscular injection, or intrathecal or intraventricular administration.

Nucleic acid molecules can be administered to cells by a variety of methods known to those of skill in the art, including, but not restricted to, encapsulation in liposomes, by ionophoresis, or by incorporation into other vehicles, such as hydrogels, biodegradable nanocapsules, and bioadhesive microspheres, or by proteinaceous vectors.

The antagomir can be administered to the subject either as a naked oligonucleotide agent, in conjunction with a delivery reagent, or as a recombinant plasmid or viral vector which expresses the oligonucleotide agent.

The miR-33 inhibitor composition can be administered to the subject by any means suitable for delivering the agent to the cells of the tissue at or near the area of unwanted miR-33 expression. For example, an MiR-33 inhibitor composition that targets miR-33 can be delivered directly to a site of inflammation, or can be conjugated to a molecule that targets the site of inflammation. Exemplary delivery methods include administration by gene gun, electroporation, or other suitable parenteral administration route.

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intra-retinal injection, or sub-retinal injection); subcutaneous injection or deposition including subcutaneous infusion (such as by osmotic pumps); direct application by a catheter or other placement device (e.g., an implant comprising a porous, non-porous, or gelatinous material).

The miR-33 inhibitor composition can be provided in sustained release composition. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained release composition may be appropriate.

The miR-33 inhibitor composition can be administered in a single dose or in multiple doses. Where the administration of the antagomir is by infusion, the infusion can be a single sustained dose or can be delivered by multiple infusions.

B. Methods of Reducing Inflammation

1. Inflammatory Disease

In some embodiment, miR-33 inhibitors can be used to reduce inflammation and treat or prevent inflammatory disease in a subject.

The inflammatory disease preferably involves chronic inflammation. In some embodiments, the inflammatory disease is an autoimmune disease.

In some embodiments, miR-33 inhibitors can be used to treat inflammation associated with cancer, atherosclerosis, ischaemic heart disease, or combinations thereof. In other embodiments, miR-33 inhibitors can be used to treat or prevent acne vulgaris, asthma, atherosclerosis, autoimmune diseases, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, and interstitial cystitis.

In some embodiments, the inflammatory disease is selected from the group consisting of rheumatoid arthritis, systemic lupus erythematosus, alopecia greata, anklosing spondylitis, antiphospholipid syndrome, autoimmune addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, deiuiatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, relapsing-remitting multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

2. M1/M2 Macrophage Polarization

In preferred embodiments, miR-33 inhibitors promote polarization of macrophages in a tissue from M1 to M2 phenotypes, thereby reducing inflammation in the tissue.

In response to cytokines and microbial products, mononuclear phagocytes express specialized and polarized functional properties. Mirroring the Th1/Th2 nomenclature, many refer to polarized macrophages as M1 and M2 cells. Classically activated M1 macrophages have long been known to be induced by IFNγ alone or in concert with microbial stimuli (e.g., LPS) or cytokines (e.g., TNF and GM-CSF). IL-4 and IL-13 were subsequently found to be more than simple inhibitors of macrophage activation and to induce an alternative M2 form of macrophage activation. M2 is a generic name for various forms of activated macrophages, excluding classic M1 cells but including cells exposed to IL-4 or IL-13, immune complexes, IL-10, glucocorticoid, or secosteroid (vitamin D3) hormones.

In general, M1 cells have an IL-12$^{high}$, IL-23$^{high}$, IL-10$^{low}$ phenotype; are efficient producers of effector molecules (reactive oxygen and nitrogen intermediates) and inflammatory cytokines (IL-1β, TNF, IL-6); participate as inducer and effector cells in polarized Th1 responses; and mediate resistance against intracellular parasites and tumors. In contrast, the various forms of M2 macrophages share an IL-12$^{low}$, IL-23$^{low}$, IL-10$^{high}$ ohenotype with variable capacity to produce inflammatory cytokines depending on the signal utilized. M2 cells generally have high levels of scavenger, mannose, and galactose-type receptors, and arginine metabolism is shifted to production of ornithine and polyamines via arginase. Differential regulation of components of the IL-1 system occurs in polarized macrophages, with low IL-1β and low caspase I, high IL-1ra, and high decoy type II receptor in M2 cells.

M1 and the various forms of M2 cells have distinct chemokine and chemokine receptor repertoires. In general, M2 cells participate in polarized Th2 reactions; promote killing and encapsulation of parasites; are present in established tumors and promote progression, tissue repair, and remodeling; and have immunoregulatory functions. Immature myeloid suppressor cells have functional properties and a transcriptional profile related to M2 cells.

C. Dosage

Certain factors may influence the dosage required to effectively treat a subject, including but not limited to the severity of the disease or disorder, previous treatments, the general health and/or age of the subject, and other diseases present. It will also be appreciated that the effective dosage of the antagomir used for treatment may increase or decrease over the course of a particular treatment. Changes in dosage may result and become apparent from the results of diagnostic assays. For example, the subject can be monitored after administering an antagomir composition. Based on information from the monitoring, an additional amount of the antagomir composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC$_{50}$s found to be effective in in vitro and in vivo animal models.

Dosage levels on the order of about 1 µg/kg to 100 mg/kg of body weight per administration are useful in the treatment of a disease. One skilled in the art can also readily determine an appropriate dosage regimen for administering the disclosed to a given subject. For example, the miR-33 inhibitor composition can be administered to the subject once, e.g., as a single injection. Alternatively, the miR-33 inhibitor composition can be administered once or twice daily to a subject for a period of from about three to about twenty-eight days, or from about seven to about ten days.

Thus, the miR-33 inhibitor composition can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of antagomir per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of antagomir per kg of bodyweight.

Delivery of an miR-33 inhibitor composition such as an antagomer directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per organ or about 0.3-3.0 mg per organ.

Where a dosage regimen comprises multiple administrations, it is understood that the effective amount of antagomir administered to the subject can include the total amount of antagomir administered over the entire dosage regimen. One skilled in the art will appreciate that the exact individual dosages may be adjusted somewhat depending on a variety of factors, including the specific antagomir being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration. For instance, oral administration would require higher dosage levels than administration by intravenous injection. Variations in these dosage levels can be adjusted using standard empirical routines of optimization, which are well-known in the art. The precise therapeutically effective dosage levels and patterns are preferably determined by the attending physician in consideration of the above-identified factors.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. Because oligonucleotide agent-mediated silencing can persist for several days after administering the antagomir composition, in many instances, it is possible to administer the composition with a frequency of less than once per day, or, for some instances, only once for the entire therapeutic regimen.

In some embodiments, a subject is administered an initial dose, and one or more maintenance doses of an miR-33 inhibitor composition. The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Following successful treatment, it may be desirable to have the patient undergo maintenance therapy to prevent the recurrence of the disease state, wherein the compound of the invention is administered in maintenance doses, ranging from 0.01 μg to 100 g per kg of body weight.

In addition to treating pre-existing diseases or disorders, the miR-33 inhibitor composition can be administered prophylactically in order to prevent or slow the onset of a particular disease or disorder. In prophylactic applications, an antagomir is administered to a patient susceptible to or otherwise at risk of a particular disorder, such as disorder associated with aberrant or unwanted expression of miR-33.

The present invention will be further understood by reference to the following non-limiting examples.

EXAMPLES

Example 1

Anti-miR33 Increases Expression of miR-33 Target Genes in the Liver, including ABCA1

Materials and Methods

Mice

All experiments were approved by the New York University School of Medicine Institutional Animal Care and Use Committee. Ldlr$^{-/-}$ mice were weaned at 4 weeks of age and placed on a high fat diet (21% (wt/wt) fat, 0.3% cholesterol; Research Diets) for 14 weeks, at which point mice were either sacrificed (baseline) or switched to chow diet for 4 weeks. Coincident with the switch to chow diet, mice were randomized into 3 groups (n=15 mice): no treatment (PBS), 2'F/MOE control anti-miR or 2'F/MOE anti-miR33 oligonucleotide (Regulus Therapeutics). Mice received 2 injections of 10 mg/kg anti-miR (or an equivalent volume of PBS) the first week, spaced two days apart, and weekly injections of 10 mg/kg anti-miR (or PBS) thereafter for 4 weeks. Following the second injection of anti-miR, mice were monitored for inflammation by measurement of serum IL-6 and MCP-1 by ELISA (eBioscience). At sacrifice, mice were anaesthetized with isofluorane, and ex-sanguinated by cardiac puncture. Mice were perfused with PBS followed by 10% sucrose in PBS. Aortic roots were embedded in OCT medium and frozen immediately, and liver tissue was snap-frozen under liquid nitrogen and stored at −80° C.

RNA Isolation and Quantitative PCR

Liver tissue was homogenized using the Bullet Blender Tissue Homogenizer (Next Advance), and total RNA was extracted using Trizol Reagent (Invitrogen). RNA integrity was verified using the Agilent Biolanalzyer prior to use. For miRNA measurements, 1 mg of total RNA was reverse transcribed using the RT$^2$ First Strand Synthesis kit (SABiosciences) and miR-33 was detected using specific primers to mmu-miR33 and normalized to U6 small RNA (SABiosciences) as described (Rayner, K. J., et al. 2010. *Science* 328:1570-1573). For all other analysis, 1 μg of total RNA was reverse-transcribed using iScript cDNA Synthesis kit (BioRad), gene expression was measured by quantitative RT-PCR, and normalized to GAPDH as described (Rayner, K. J., et al. 2010. *Science* 328:1570-1573; Stewart, C. R., et al. 2010. *Nat Immunol* 11:155-161).

Western Blotting

Protein was extracted from liver using the Bullet Blender in RIPA buffer, according to the manufacturer's protocol. For detection of ABCA1 and ABCG1, 40 μg of protein was separated on a 6% SDS-PAGE gel and transferred to nitrocellulose. Membranes were incubated overnight with antibodies to ABCA1 or ABCG1 (Abeam) and proteins were visualized using appropriate secondary antibodies conjugated to IR-dyes (Rockland) and scanned using the Odyssey Imaging System (Licor) as described (Rayner, K. J., et al. 2010. *Science* 328:1570-1573). ABCA1 and ABCG1 protein expression was quantified and normalized to tubulin detected using an Ab from Sigma. For detection of apoA1 and apoE in HDL containing FPLC fractions, 10 μl of pooled fractions were separated on a 10% SDS-PAGE gel and transferred to PVDF. Membranes were incubated overnight with antibodies to apolipoprotein A1 (Abeam), or apolipoprotein E (R & D Systems) and antibody reactivity detected as described above.

Results

The subcutaneous or intraperitoneal delivery of 2' fluoro/methoxyethyl (2'F/MOE) modified phosphorothioate backbone anti-sense oligonucleotides has been used successfully in mice to inhibit the function of various miRNAs and to increase expression of their target gene, with no apparent toxicity (Davis, S., et al. 2009. *Nucleic Acids Res* 37:70-77). Similar anti-miRNA strategies have been shown to be well tolerated in non-human primates (Elmen, J., et al. 2008. *Nature* 452:896-899; Lanford, R E., et al. 2010. *Science* 327:198-201), indicating that these anti-sense oligonucleotides may be promising therapeutic agents. To assess the effects of inhibiting miR-33 in a model of established atherosclerosis, Ldlr$^{-/-}$ mice were first fed a western diet for 14 weeks (baseline), after which they were switched to a chow diet to block atherosclerosis progression and injected subcutaneously with 10 mg/kg of 2'F/MOE anti-miR33 or control anti-miR oligonucleotides, or PBS (untreated). To maximize anti-miR delivery, mice were injected twice weekly the first week, then once weekly thereafter for a total of four weeks. Consistent with previous studies (Henry, S., et al. 2000. *J Pharmacol Exp Ther* 292:468-479), this regimen did not induce a detectable immune response, as serum levels of interleukin-6 (IL-6) and monocyte chemoattractant protein- (MCP-1) in mice treated with either control anti-miR or anti-miR33 did not differ from mice injected with PBS alone.

Figure 1B:
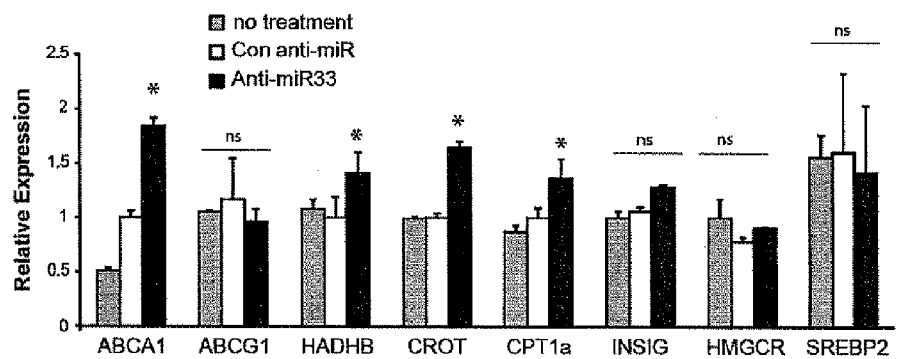
FIG. 1B is a bar graph showing mRNA expression of ABCA1, ABCG1, HADHB, CROT, CPT1a, INSIG, HMGCR, and SREBP2 following anti-miR33 treatment (right bars) compared to no treatment (left bars), or control anti-miR (middle bars).
Figure 1C:
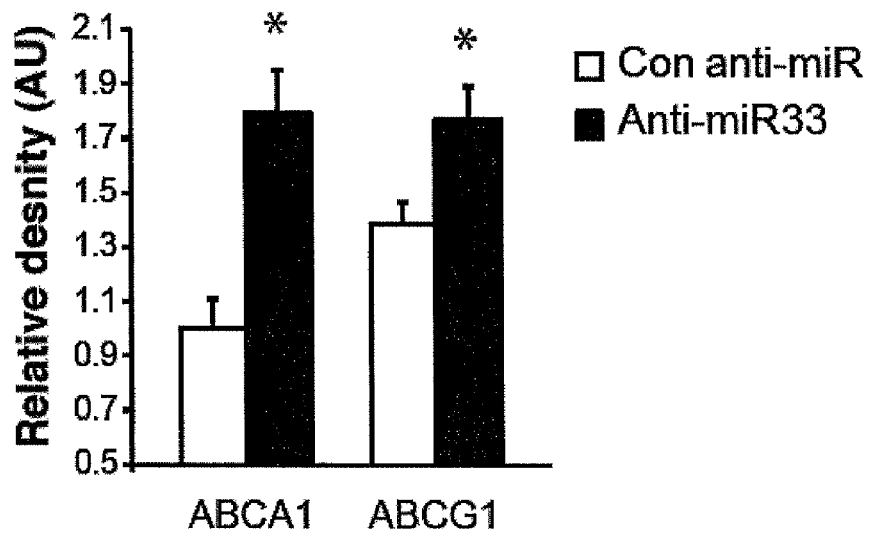
FIG. 1C is a bar graph showing ABCA1 (left set of bars) and ABCG1 (right set of bars) protein expression (relative density) in mice treated with anti-miR33 (solid bars) compared to controls (open bars).

To determine the efficacy of anti-miR33 treatment, we measured the expression of miR-33 and its target genes in the livers of mice after 4 weeks of treatment. Levels of miR-33 detected by quantitative RT-PCR were decreased by more than 60% in anti-miR33 treated mice compared to mice receiving control anti-miR (FIG. 1A). Consistent with this, the expression of ABCA1 in the liver was increased or "de-repressed" in the anti-miR33 treated group compared to untreated or control anti-miR treated mice, however no change in ABCG1 mRNA was observed (FIG. 1B). Furthermore, both ABCA1 and ABCG1 protein was increased in the livers of anti-miR33 treated mice, compared to control groups (FIG. 1C). To confirm the specificity of anti-miR33 action, we examined the expression of other hepatic lipid metabolism genes. While there were no significant changes in genes lacking functional miR-33 target sites (i.e. Insig, Hmgcr and Srebf2), the expression of other known miR-33 target genes involved in fatty acid metabolism were significantly increased with anti-miR33 treatment (Crot, Hadhb, Cpt1a) (FIG. 1B). Together these data demonstrate that 2'F/MOE anti-miR33 effectively inhibits miR-33 activity and selectively increases expression of genes repressed by miR-33.

Example 2

Anti-miR33 Treatment Increases HDL and Enhances Reverse Cholesterol Transport In vivo Materials and Methods Plasma Lipoprotein Analysis Plasma was collected at sacrifice and total cholesterol was assayed (1:5 dilution) using the Cholesterol-E kit (Wako) as described (28). For FPLC analysis, 300 µl of pooled plasma (n=8 mice total) was separated on a Superose column (Amersham) at a flow rate of 0.4 ml/min as described (Rayner, K J., et al. 2010. *Science* 328:1570-1573). Fractions were collected and analyzed for total cholesterol content using the Cholesterol-E kit. For HDL measurements, apoB-containing lipoproteins were precipitated by the phosphotungstate-magnesium method, and HDL cholesterol was measured using either the HDL Cholesterol kit (Wako) or the Amplex Red Cholesterol Assay (Invitrogen) (Rayner, K. J., et al. 2010. *Science* 328:1570-1573).

In vivo Reverse Cholesterol Transport Assay

Bone marrow derived macrophages were prepared from C57Bl/6 mice as previously described (Stewart, C. R., et al. 2010. *Nat Immunol* 11:155-161). Bone marrow was isolated and cells were plated overnight in DMEM supplemented with 10% FBS and 15% L-929 conditioned media. Non-adherent cells were removed and cultured for an additional 6 days to allow for macrophage differentiation. For RCT assays, BMDMs were washed twice and incubated with 37.5 µg/ml acLDL and 5 µCi/ml $^3$H-cholesterol for 24 hours as described (Zhang, Y., et al. 2005. *The Journal of Clinical Investigation* 115:2870-2874; Wang, X., et al. 2007. *The Journal of Clinical Investigation* 117:2216-2224). Cells were resuspended in ice-cold DMEM and 2–3×10$^6$ cells were injected subcutaneously into individually-housed mice fed a WD diet and treated with either control anti-miR or anti-miR33 for 4 weeks as described above. Prior to injection, an aliquot of cells was counted using liquid scintillation counting to measure baseline radioactivity. Blood was obtained by saphenous vein puncture at 6 and 24 hours after BMDM injection, and by cardiac puncture after 48 hours at sacrifice. An aliquot of plasma was used for liquid scintillation counting immediately at each time point. Feces were collected for 24 and 48 hours post-injection, and homogenized in 50% NaOH overnight, after which an aliquot was used for liquid scintillation counting. At sacrifice, liver samples were collected and incubated with hexane:isopropanol (3:2) for 48 hours, then dried overnight. Lipids were re-solubilized in liquid scintillation fluid and radioactivity was counted. Reverse cholesterol transport to plasma, feces and liver was calculated as a % of total radioactivity injected at baseline.

Results

Figure 2A:
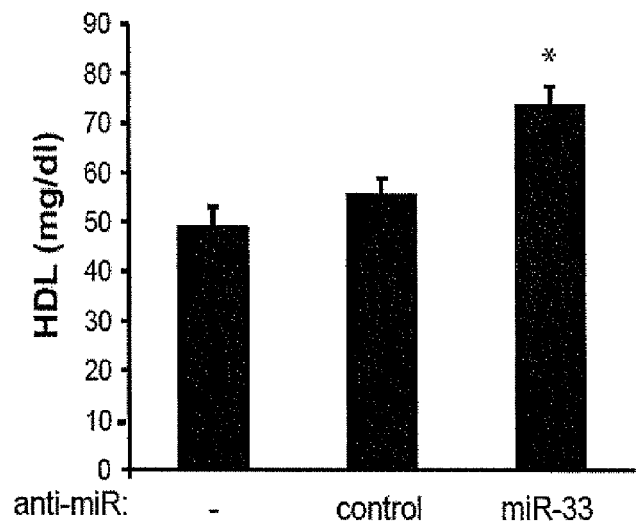
FIG. 2A is a bar graph showing HDL levels (mg/dl) after 4 weeks with PBS (no treatment, first bar), control anti-miR (second bar) and anti-miR33 (third bar).
Figure 2B:
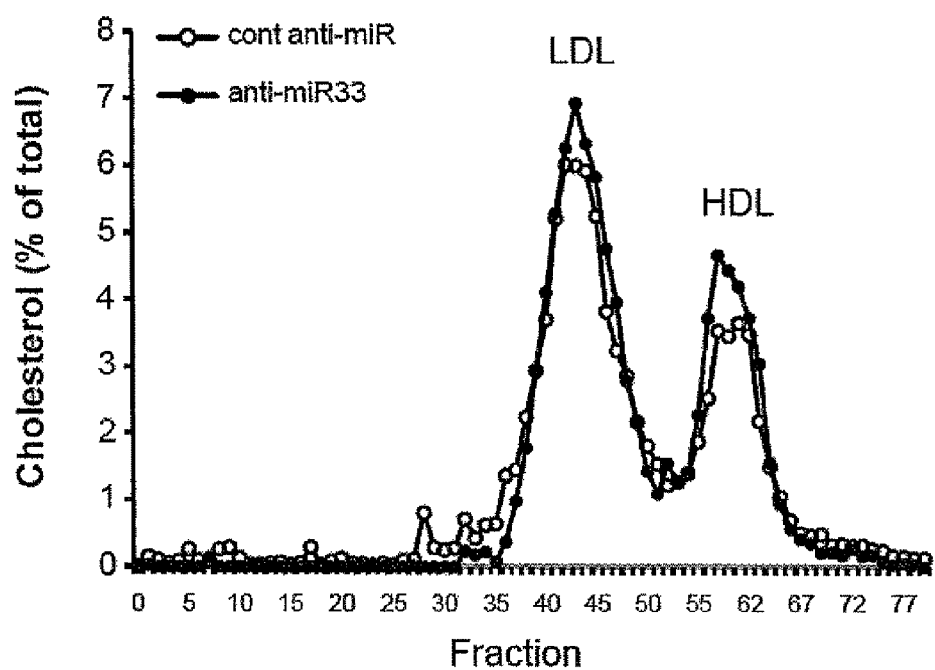
FIG. 2B is a bar showing FPLC profiles of control anti-miR (open circles) and anti-miR33 (closed circles) treated mice.

As increased ABCA1 expression in the liver would be predicted to augment HDL biogenesis, we measured circulating total and HDL cholesterol levels in the anti-miR33 and control anti-miR treated mice. Consistent with previous work by our lab and others showing that short-term (5-12 days) inhibition of miR-33 in C57BL6 mice results in 25-30% increases in circulating HDL (2830), treatment of Ldlr$^{-/-}$ mice with anti-miR33 for 4 weeks raised HDL-C by 35% compared to control mice (FIG. 2A). By contrast, there was no difference in total circulating cholesterol between mice that were treated with control anti-miR, anti-miR33 or PBS (Table 1). Analysis of lipoproteins by FPLC showed an increase in cholesterol content of the HDL fractions (fractions 54-67) of the anti-miR33 compared to control anti-miR treated mice (FIG. 2B). To test if antimiR33 treatment altered the apolipoprotein content on HDL particles, we measured apoA1 and apoE in the HDL fractions by western blotting. In anti-miR33 treated mice, there is an overall increase in apoA1 and apoE recovered in the HDL fractions compared to control anti-miR treated mice. Moreover, a higher proportion of apoA1 was associated with larger HDL particles, consistent with increased efflux of cholesterol from cells to HDL from peripheral tissues.

TABLE 2

Plasma lipid and body weight parameters.

| Parameter | baseline | PBS | control anti-miR | anti-miR33 |
|---|---|---|---|---|
| Body weight (g): at start | — | 27.4 ± 2.1 | 30.4 ± 2.2 | 31.5 ± 2.5 |
| at sacrifice | 27.2 ± 2.0 | 26.6 ± 0.65 | 24.5 ± 1.4 | 24.9 ± 1.6 |
| Total cholesterol (mg/dl) | 1089 ± 162 | 264 ± 40 | 250 ± 46 | 272 ± 45 |
| Plasma triglyceride (mg/dl) | 263.8 ± 34 | 56.5 ± 15 | 64.9 ± 19 | 71.2 ± 18 |

Body weight was obtained at baseline (after 14w WD) and at sacrifice (after 4 weeks treatment with PBS, control anti-miR or anti-miR33). Total plasma cholesterol and triglycerides were obtained at sacrifice. All data expressed as mean ± SD, n = 15 mice/group.

Figure 3A:
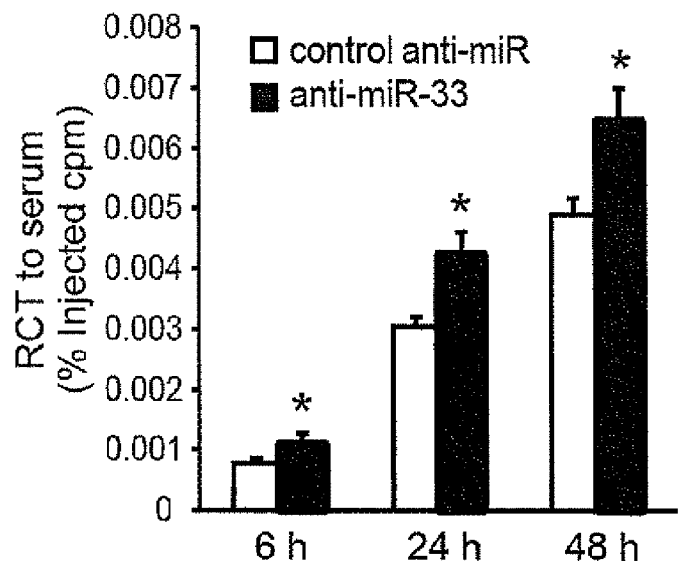
FIG. 3A-3C are bar graphs showing reverse cholesterol transport (RCT, % injected cpm) to serum (FIG. 3A), liver (FIG. 3B), and feces (FIG. 3C) measured at 6 h (first set of bars), 24 h (second set of bars) and 48 h (third set of bars) after $^3$H-cholesterol labeled macrophage injection in anti-miR33 treated mice (solid bars) compared to controls (open bars).
Figure 3B:
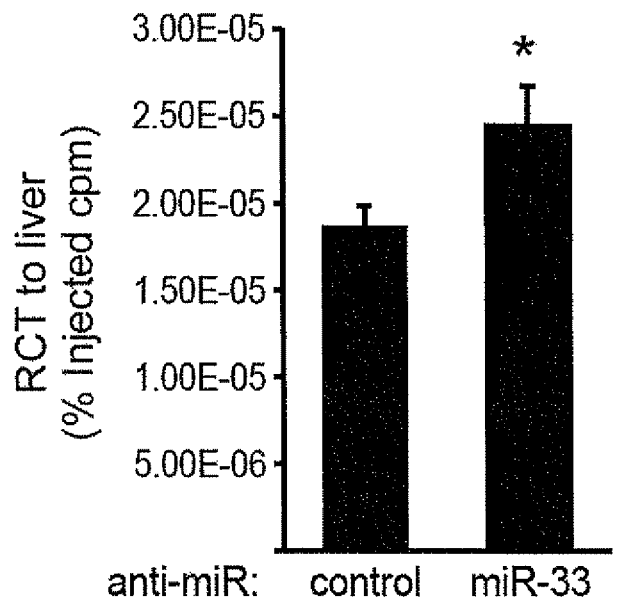
Figure 3C:
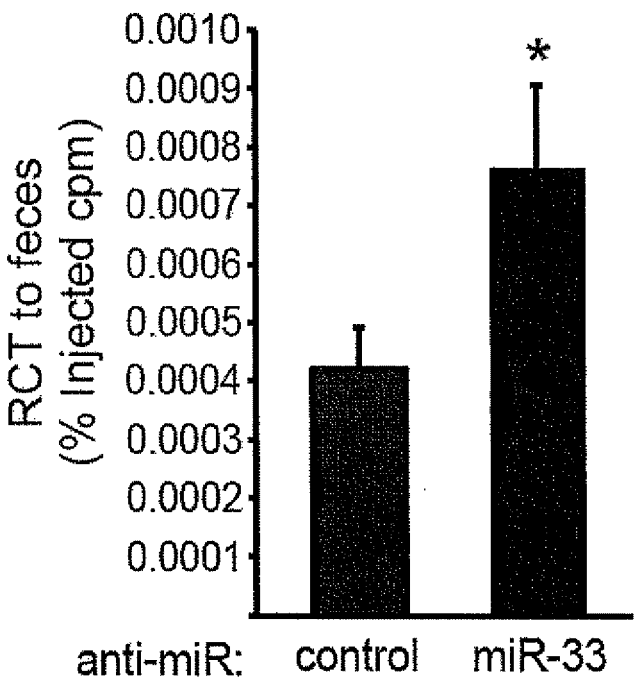

To determine whether higher HDL levels in response to anti-miR33 treatment up-regulates cholesterol transport from peripheral cells to the liver for further excretion into bile and feces, we performed an in vivo reverse cholesterol transport (RCT) assay that traces $^3$H-cholesterol from macrophages loaded with cholesterol ex vivo (Zhang, Y., et al. 2005. *J. Clin. Invest.* 115:2870-2874; Wang, X., et al. 2007. *J. Clin. Invest.* 117:2216-2224). Anti-miR33 treated mice injected subcutaneously with cholesterol loaded/$^3$H-cholesterol-labeled bone marrow derived macrophages showed a 35-40% increase in the appearance of $^3$H-cholesterol to plasma over 48 h, compared to control mice (FIG. 3A). Furthermore, anti-miR33 treated mice showed a 42% increase in the delivery of $^3$H-tracer to the liver (FIG. 3B) and an 82% increase in $^3$H-sterols excreted into feces (FIG. 3C). Together, these results establish that miR-33 inhibition not only increases circulating HDL, but enhances the RCT pathway by which excess cholesterol is effluxed from peripheral tissues, a process that is particularly important in the removal of cholesterol from atherosclerotic lesions.

Example 3

Anti-miR33 Treatment Induces Atherosclerosis Regression and Lesion Remodeling

Materials and Methods
Atherosclerosis Analysis

Hearts embedded in OCT were sectioned through the aortic root (8 µm), and stained with hematoxylin and eosin for lesion quantification or used for immunohistochemical analysis as previously described (Moore, K. J., et al. 2005. *J Clin Invest* 115:2192-2201; Manning-Tobin, J. J., et al. 2009. *Arterioscler Thromb Vasc Biol* 29:19-26). For morphometric analysis of lesions, 16 sections per mouse were imaged, spanning the entire aortic root, and lesions were quantified using iVision Software. For collagen analysis, 10 sections per mouse were stained with Picrosirius Red and imaged under polarized light using a Zeiss Axioplan microscope. For detection of neutral lipid, oil red O staining was performed as previously described (Moore, K. J., et al. 2005. *J Clin Invest* 115:2192-2201; Manning-Tobin, J. J., et al. 2009. *Arterioseler Thromb Vasc Biol* 29:19-26). For macrophage analysis, 10 sections per mouse were incubated with an anti-CD68 antibody (rat anti-mouse CD68, 1:500, Serotec) and a secondary antibody conjugated to biotin (1:500) and antibody reactivity was visualized using the Vectastain ABC Elite kit (Vector labs) and diaminobenzadine (DAB; Sigma). For detection of 2'F/MOE oligonucleotides frozen sections were fixed in neutral buffered foiuialin at room temperature, and treated with Dako Dual Endogenous Enzyme-Blocking Reagent (DAKO, Carpinteria, Calif.) for 5 minutes. Slides were rinsed in PBS and blocked with 5% normal donkey serum, followed by incubation with primary antibodies raised against the phosphorothioate backbone of the 2'F/MOE oligonucleotides or a control antibody for 1 hour. Slides were incubated with HRP conjugated donkey anti-rabbit secondary antibody for 30 minutes, and immunoreactivity was visualization with DAB substrate (DAKO).

Laser Capture Microdissection

Laser capture microdissection was performed using a PixCell II instrument (Arcturus Bioscience, Mountain View, Calif.) as previously described (Trogan, E., et al. 2002. *Proc Natl Acad Sci USA* 99:2234-2239; Trogan, E., et al. 2005. *Methods Mol Biol* 293:221-231). To visualize CD68-positive cells, a guide slide was prepared by staining for CD68 as described above. Cells corresponding to CD68+ area in serial sections were collected and RNA was extracted using the Arcturus Picopure RNA Isolation kit. Total RNA was amplified using the Ovation WT Pico Amp kit (NuGen), purified using Qiaquick PCR Purification kit (Qiagen) and used for quantitative PCR as described above.

Affymetrix Gene Array Analysis

Messenger RNA from macrophages collected by laser capture microdissection were profiled for expression on Affymetrix Mouse 430 2.0 arrays in quadruplicates. Macrophages were derived from three groups of mices: (1) anti-miR33 treated, (2) control anti-miR treated, and (3) untreated. Microarray data was RMA normalized (Bolstad, B. M., et al. 2003. *Bioinformatics* 19:185-193), log 2 transformed, and quality controlled by principal component analysis (PCA). The gene-level array data was then compared between treated vs untreated groups by one-way ANOVA. The genes were then split between those containing one or more mir-33 seed-matched heptamers (nucleotides 1-7 or 2-8) in their 3'UTRs and those that contained none. The R package [ref: http://www.r-project.org/] was used to compute the cumulative distribution function (CDF) for the fold changes of these genes. Statistical significance of the shift between these two populations was determined by using a 1 sided Kolmogorov-Smirnov (KS) test.

Statistical Analyses

For atherosclerosis and immunohistochemical analyses, all comparisons were made using a one-way ANOVA (p<0.05) and data are expressed as mean±SEM, unless otherwise noted.

Results

Figure 4:
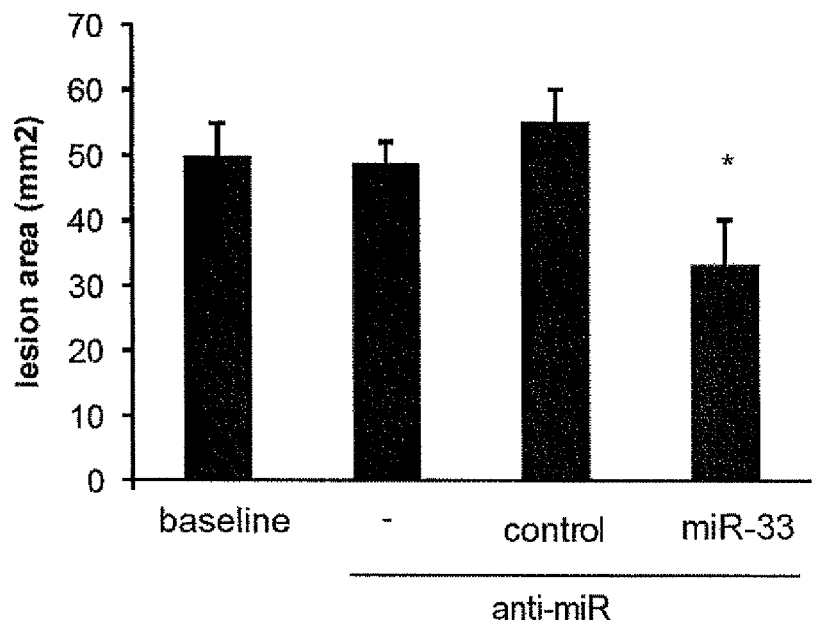
FIG. 4 is a bar graph showing lesion area (mm$^2$) from mice at baseline (first bar, after 14 w Western diet) and after 4 weeks with PBS (second bar), control anti-miR (third bar), or anti-miR33 (fourth bar) treatment.
Figure 5A:
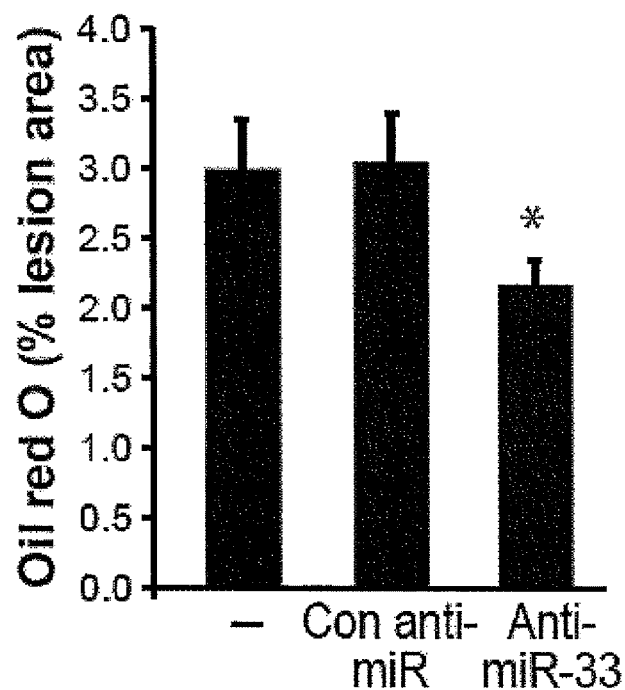
FIG. 5A is a bar graph showing oil red 0 staining for neutral lipids (% lesion area) in mice after treatment with PBS (first bar), control anti-miR (second bar), and anti-miR33 (third bar) for 4 weeks.
Figure 5B:
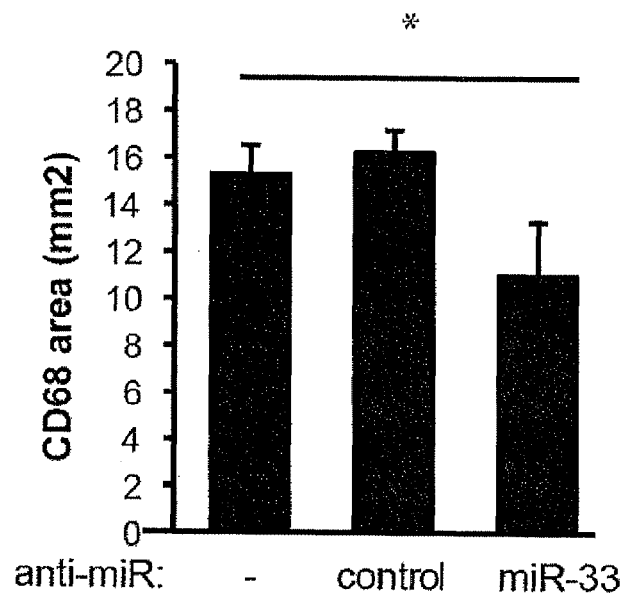
FIG. 5B is a bar graph showing CD68-positive area (mm$^2$) in mice after treatment with PBS (first bar), control anti-miR (second bar), and anti-miR33 (third bar) for 4 weeks.
Figure 5C:
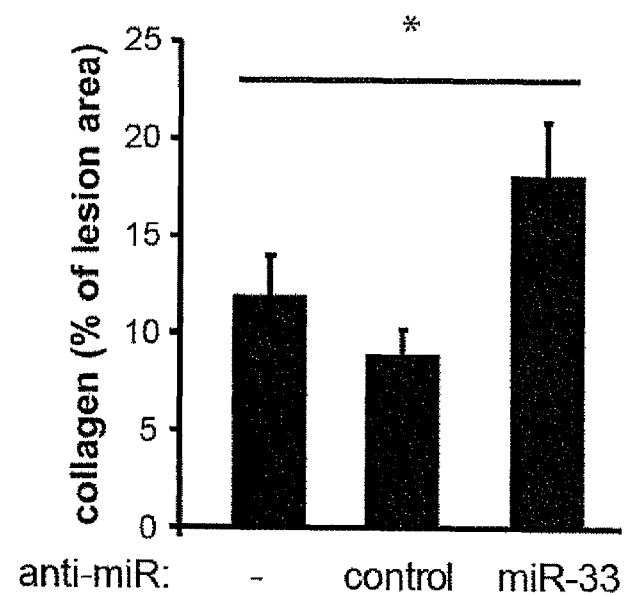
FIG. 5C is a bar graph showing collagen staining (% of lesion area) in PBS (first bar), control anti-miR (second bar), and anti-miR33 (third bar) treated mice.
Figure 6:
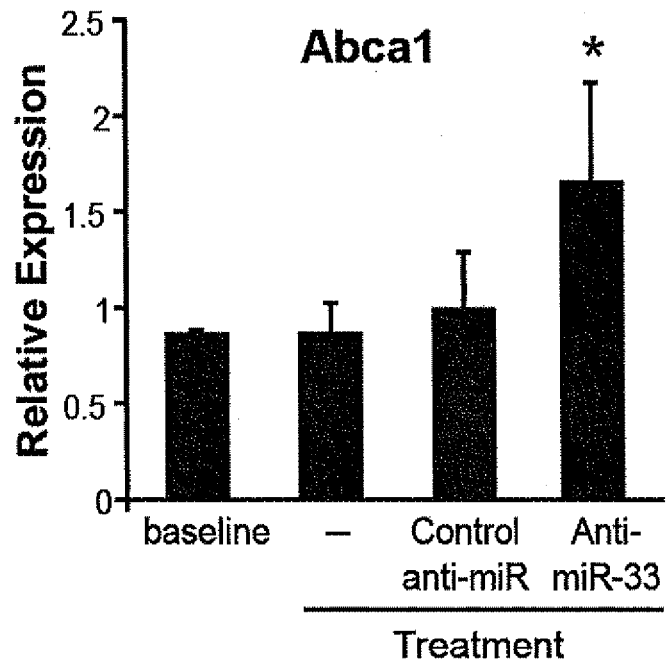
FIG. 6 is a bar graph showing relative expression of Abca1 mRNA in plaque CD68+ macrophages that were isolated by laser capture microdissection from mice treated with PBS, control anti-miR, or miR-33 compared to baseline, and analyzed by qRT-PCR analysis. *p≤0.05 compared to all other groups.

Data from mouse models of apoA1 overexpression or HDL infusion suggest that raising HDL-C favorably impacts atherosclerosis (Rubin, E. M., et al. 1991. *Nature* 353:265-267; Paszty, C., et al. 1994. *J Clin Invest* 94:899-903; Plump, A. S., et al. 1994. *Proc Natl Acad Sci USA* 91:9607-9611; Rong, J. X., et al, 2001. *Circulation* 104:2447-2452). We thus hypothesized that the enhanced RCT in anti-miR33 treated mice would promote removal of cholesterol from vessel wall foam cells, leading to plaque regression. The mean aortic sinus lesion area of Ldlr$^{-/-}$ mice injected for 4 weeks with either PBS (untreated) or control anti-miR did not differ from that of mice harvested after 14 weeks of WD feeding (baseline) (FIG. 4). By contrast, anti-miR33 treated mice had a 35% reduction in lesion area in the aortic sinus compared to baseline and control groups (FIG. 4). Quantification of lipid accumulation in aortic sinus lesions by oil red 0 staining demonstrated a corresponding 28% decrease in lipid in anti-miR33 treated mice compared to controls (FIG. 5A). Moreover, there was a 35% reduction in CD68+ macrophage content (FIG. 5B), and a 2-fold increase in total lesional collagen content in anti-miR33 treated mice compared to controls (FIG. 5C), indicating remodeling of plaques towards a more stable phenotype. Together, these results indicate that anti-miR33 treatment supports the efflux of cholesterol from the lesional macrophages and promotes regression of established atherosclerosis.

Figure 8A:
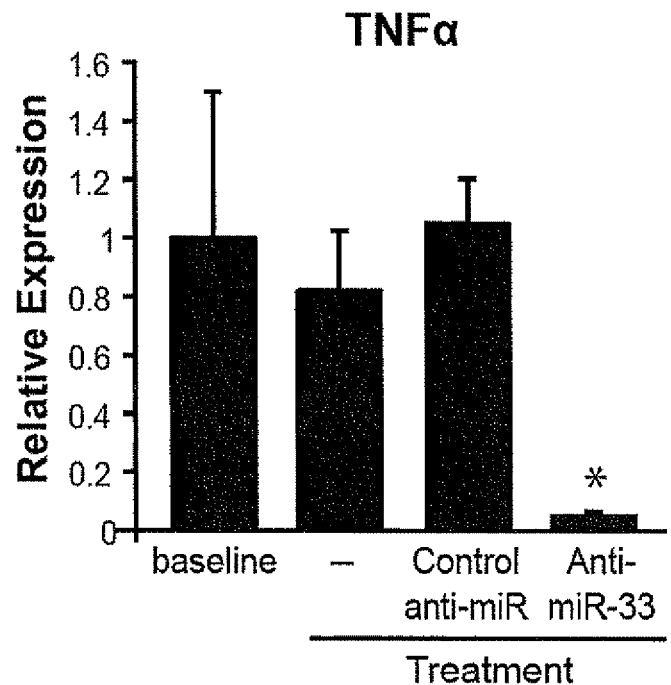
FIGS. 8A to 8F are bar graphs showing relative expression of TNFα (FIG. 8A), TLR6 (FIG. 8B), TLR13 (FIG. 8C) iNos (FIG. 8D), Arg1 (FIG. 8E) and IL-10 (FIG. 8F) in lesional CD68+ macrophages laser captured from aortic sinus lesions of Ldlr-/- mice treated with PBS, control anti-miR, or miR-33 compared to baseline. Data are the mean expression levels from 4 mice per group±SEM. *p<0.05, compared to baseline.
Figure 8B:
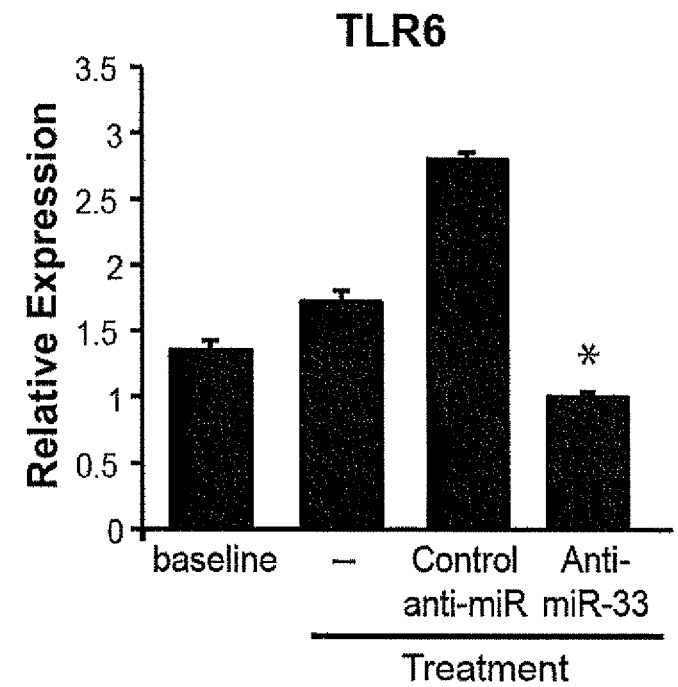
Figure 8C:
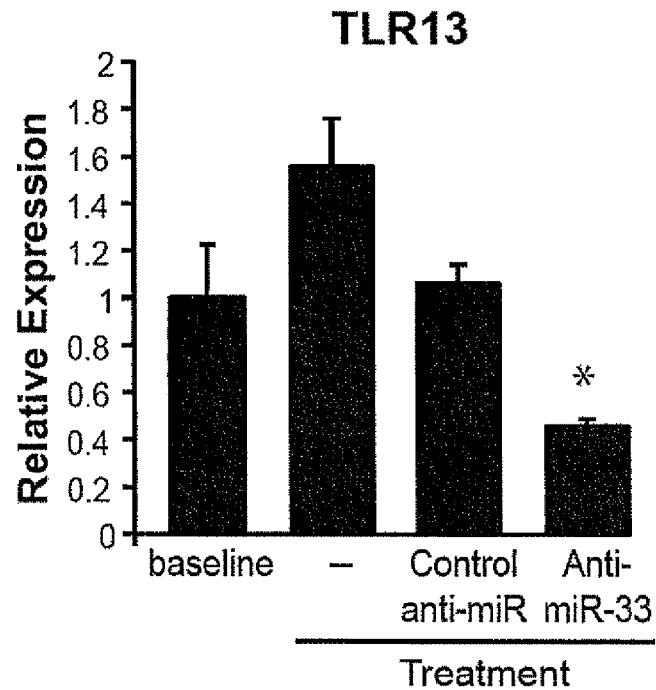
Figure 8D:
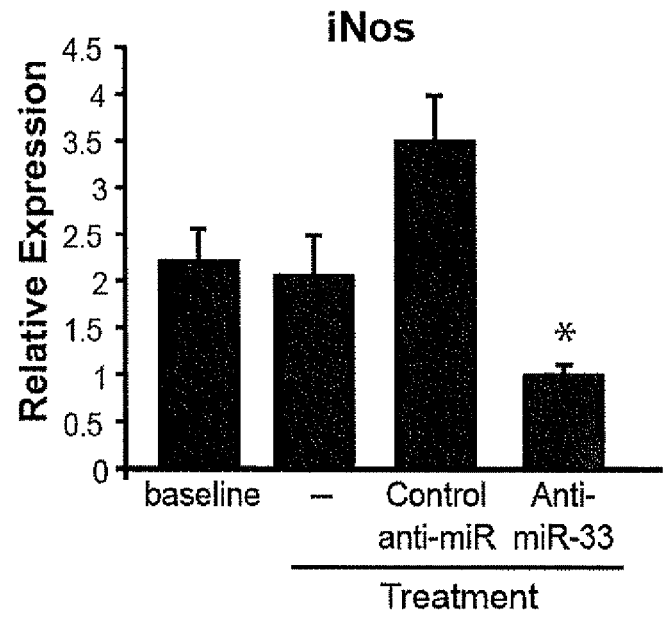
Figure 8E:
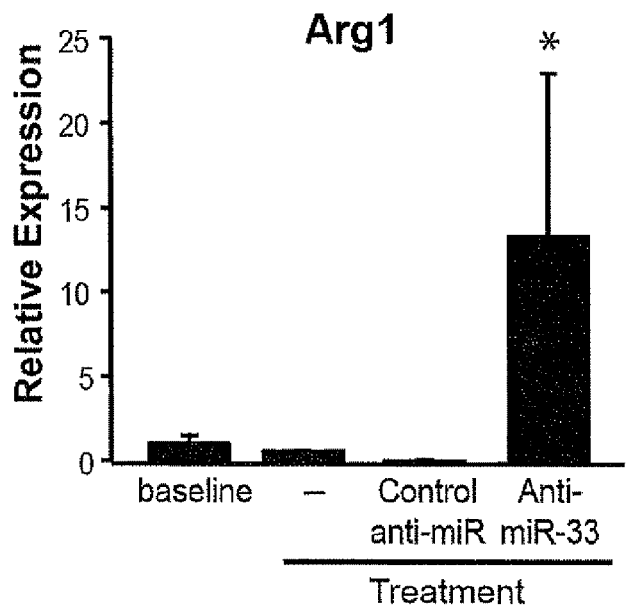
Figure 8F:
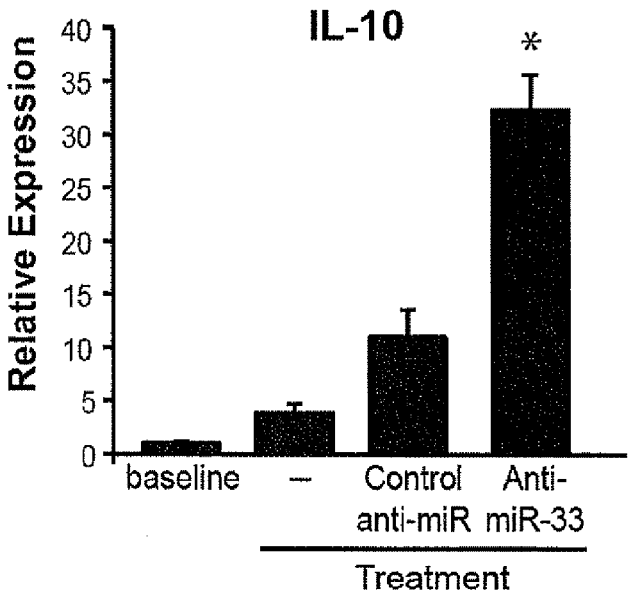
Figure 9A:
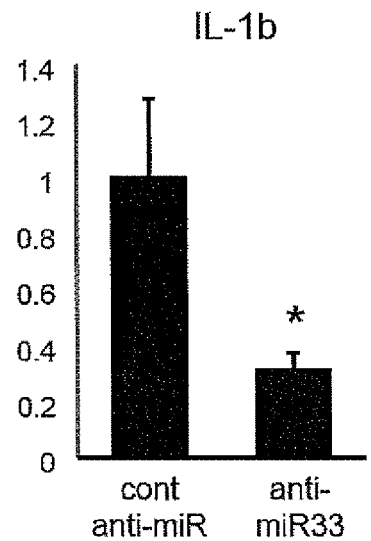
FIGS. 9A to 9F are bar graphs showing relative expression of IL-1b (FIG. 9A), TNFa (FIG. 9B), Arg1 (FIG. 9C), IL-4 (FIG. 9D), Fizz1 (FIG. 9E), IL-10 (FIG. 9F) in peritoneal macrophages transfected with anti-miR-33 (right bar) or control anti-miR (left bar).
Figure 9B:
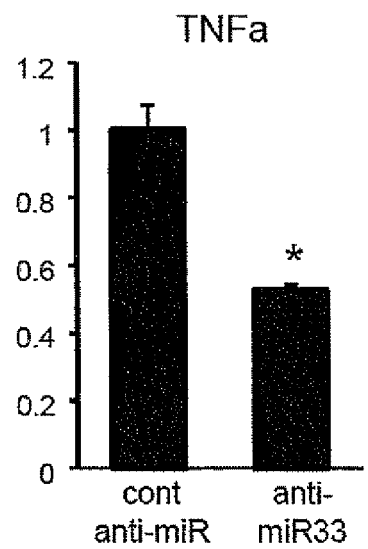
Figure 9C:
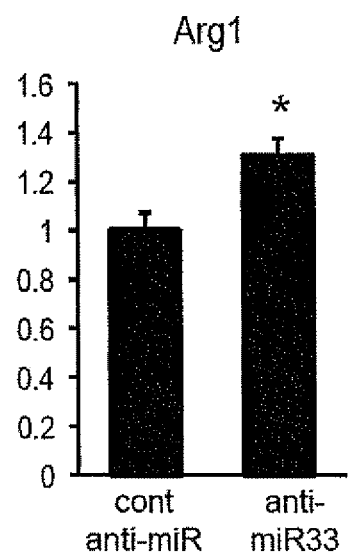
Figure 9D:
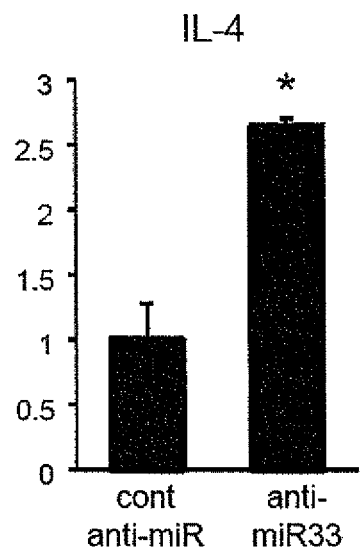
Figure 9E:
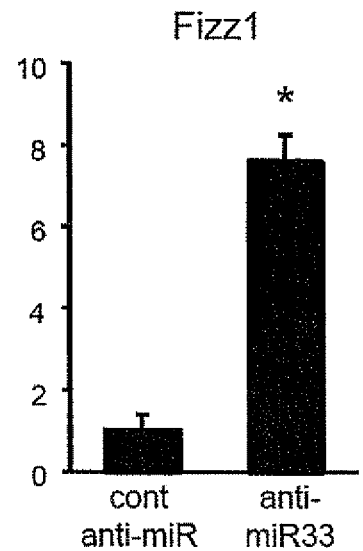
Figure 9F:
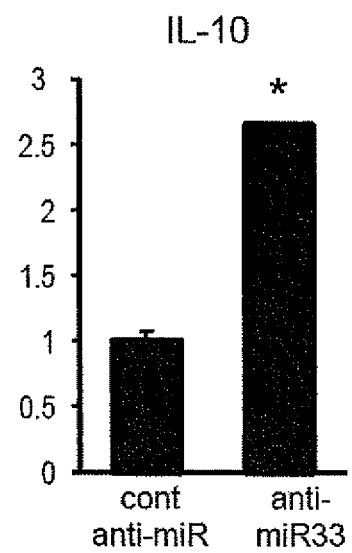

Quantitative PCR confirmed downregulation of several of these inflammatory genes in lesional macrophage of anti-miR33 treated mice, including TNFα and Toll-like receptors 6 and 13 (FIG. 8A). Recent evidence suggests that regressing atherosclerotic lesions contain a greater proportion of macrophages characterized by the reparative M2 phenotype compared to the pro-inflammatory M1 macrophages, and that HDL can promote regression in part by enhancing this pathway. In accordance with this, we find that lesional macrophages from antimiR33 treated mice show increased mRNA levels of anti-inflammatory M2 markers (Arg1, IL-10) and reduced expression of pro-inflammatory M1 markers (iNos and TNFα [consistent with the array results]). Overall, these gene expression analyses suggest that in addition to containing less lipid and increased markers of plaque stability, macrophages from within the lesions of antimiR33 treated mice have a less inflammatory and more reparative phenotype.

Example 4

Evaluation of Anti-miRNA Molecule Delivery to Macrophages

Materials and Methods
Atherosclerosis Analysis

Hearts embedded in OCT were sectioned through the aortic root (8 μm), and stained with hematoxylin and eosin for lesion quantification or used for immunohistochemical analysis as previously described (Moore, K. J., et al. 2005. *J Clin Invest* 115:2192-2201; Manning-Tobin, J. J., et al. 2009. *Arterioscler Thromb Vasc Biol* 29:19-26). For morphometric analysis of lesions, 16 sections per mouse were imaged, spanning the entire aortic root, and lesions were quantified using iVision Software. For collagen analysis, 10 sections per mouse were stained with Picrosirius Red and imaged under polarized light using a Zeiss Axioplan microscope. For detection of neutral lipid, oil red O staining was performed as previously described (Moore, K. J., et al. 2005. *J Clin Invest* 115:2192-2201; Manning-Tobin, J. J., et al. 2009. *Arterioscler Thromb Vasc Biol* 29:19-26). For macrophage analysis, 10 sections per mouse were incubated with an anti-CD68 antibody (rat anti-mouse CD68, 1:500, Serotec) and a secondary antibody conjugated to biotin (1:500) and antibody reactivity was visualized using the Vectastain ABC Elite kit (Vector labs) and diaminobenzadine (DAB; Sigma). For detection of 2'F/MOE oligonucleotides frozen sections were fixed in neutral buffered formalin at room temperature, and treated with Dako Dual Endogenous Enzyme-Blocking Reagent (DAKO, Carpinteria, Calif.) for 5 minutes. Slides were rinsed in PBS and blocked with 5% normal donkey serum, followed by incubation with primary antibodies raised against the phosphorothioate backbone of the 2'F/MOE oligonucleotides or a control antibody for 1 hour. Slides were incubated with HRP conjugated donkey anti-rabbit secondary antibody for 30 minutes, and immunoreactivity was visualization with DAB substrate (DAKO).

Laser Capture Microdissection

Laser capture microdissection was performed using a PixCell II instrument (Arcturus Bioscience, Mountain View, Calif.) as previously described (69, 70). To visualize CD68-positive cells, a guide slide was prepared by staining for CD68 as described above. Cells corresponding to CD68+ area in serial sections were collected and RNA was extracted using the Arcturus Picopure RNA Isolation kit. Total RNA was amplified using the Ovation WT Pico Amp kit (NuGen), purified using Qiaquick PCR Purification kit (Qiagen) and used for quantitative PCR.

Quantitative PCR

1 μg of total RNA was reverse-transcribed using iScript cDNA Synthesis kit (BioRad), gene expression was measured by quantitative RT-PCR, and normalized to GAPDH as described (Rayner, K. J., et al. 2010. *Science* 328:1570-1573; Stewart, C. R., et al. 2010. *Nat Immunol* 11:155-161).

Results

To test whether miR-33 antisense oligonucleotides can be delivered to macrophages within an atherosclerotic plaque to directly alter target gene expression in these cells, immunohistochemical staining of aortic sinus lesions was performed to determine the localization of miR-33 antisense oligonucleotide.

Aortic sinus lesions, isolated from the mice described in Example 8, were subjected to immunohistochemical staining using an antibody directed against the phosphorothioate backbone of the miR-33 antisense oligonucleotide. It was observed that the miR-33 antisense oligonucleotide was found within the plaque, where it co-localized with CD68-positive macrophages. To determine whether the miR-33 antisense oligonucleotide affects target gene expression within the plaque, lesional CD68+ macrophages were isolated using laser-capture microdissection and RNA was extracted for gene expression analysis. Examination of ABCA1 expression levels in lesional macrophages demonstrated similar levels of Abca1 mRNA in baseline, PBS or control anti-miR treated mice. Notably, miR-33 antisense oligonucleotide treated mice had a 66% increase in lesional macrophage ABCA1 expression compared to the control groups (FIG. 20). These results demonstrate that the miR-33 antisense oligonucleotides are capable of penetrating the atherosclerotic lesion to reach plaque macrophages, where they can directly alter target gene expression.

Example 5

Gene Expression Profiling in Lesional Macrophages

Materials and Methods
Affymetrix Gene Array Analysis

Messenger RNA from macrophages collected by laser capture microdissection were profiled for expression on Affymetrix Mouse 430 2.0 arrays in quadruplicates. Macrophages were derived from three groups of mices: (1) anti-miR33 treated, (2) control anti-miR treated, and (3) untreated. Microarray data was RMA normalized (Bolstad, B. M., et al. 2003. *Bioinformatics* 19:185-193), log 2 transformed, and quality controlled by principal component analysis (PCA). The gene-level array data was then compared between treated vs untreated groups by one-way ANOVA. The genes were then split between those containing one or more mir-33 seed-matched heptamers (nucleotides 1-7 or 2-8) in their 3'UTRs and those that contained none. The R package [ref: http://www.r-project.org/] was used to compute the cumulative distribution function (CDF) for the fold changes of these genes. Statistical significance of the shift between these two populations was determined by using a 1-sided Kolmogorov-Smirnov (KS) test.

Results

Figure 7:
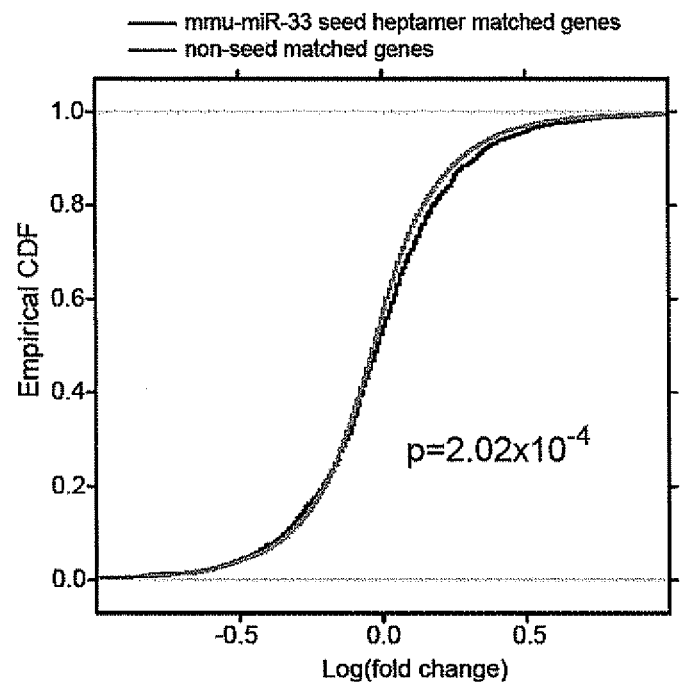
FIG. 7 is graph showing cumulative distribution function (CDF) for mRNA of lesional macrophages isolated by laser capture in anti-miR33 (black line) treated mice compared to control anti-miR (gray line) treated mice.

To further understand the impact of the inhibition of miR-33 on plaque macrophage phenotype gene expression profiling was performed on RNA isolated from lesional macrophages using Affymetrix gene arrays. Cumulative distribution function analysis revealed that treatment with miR-33 antisense oligonucleotide resulted in a statistically significant enrichment in the expression of genes containing miR-33 binding sites in their 3' UTR compared to non-miR33 target genes (FIG. 7; $p=2.02\times10^{-4}$), consistent with specific derepression of miR-33 targets in lesional macrophages.

In addition, gene ontology analysis showed a significant downregulation in genes involved in the immune response in plaque macrophages from anti-miR33 compared to control anti-miR treated mice (Benjamini corrected p-value=$8.1\times 10^{-3}$). Quantitative PCR confirmed downregulation of several of these inflammatory genes in lesional macrophage of anti-miR33 treated mice, including TNFα and Toll-like receptors 6 and 13 (FIGS. 8A-8F). Recent evidence suggests that regressing atherosclerotic lesions contain a greater proportion of macrophages characterized by the reparative M2 phenotype compared to the pro-inflammatory M1 macrophages, and that HDL can promote regression in part by enhancing this pathway. In accordance with this, lesional macrophages from anti-miR33 treated mice showed increased mRNA levels of anti-inflammatory M2 markers (Arg1, IL-10) and reduced expression of pro-inflammatory M1 markers (iNos and INFα [consistent with the array results]). Overall, these gene expression analyses indicate that in addition to containing less lipid and increased markers of plaque stability, macrophages from within the lesions of anti-miR33 treated mice have a less inflammatory and more reparative phenotype.

Example 6

In Vitro Evidence of Anti-Inflammatory Effects of Anti-miR-33

To directly assess the effects of anti-miR-33 on inflammation, primary mouse peritoneal macrophages were transfected with anti-miR-33 or control anti-miR and markers of M1 "inflammatory" and M2 "anti-inflammatory" macrophages were measured. Peritoneal macrophages transfected with anti-miR-33 showed reduced expression of M1 markers of inflammation (IL-1 and TNFα) and an increase in M2 markers (Arg1, IL-10, IL-4 and Fizz1) (FIGS. 9A-9F). These data are consistent with anti-miR-33 inducing polarization of macrophages from a pro-inflammatory M1 state to a reparative M2 state. Notably, both Arg1 and IL-10 contain a single miR-33 binding site in their 3'UTRs and as such, the increase in Arg1 and IL-10 mRNA in lesional macrophages of anti-miR-33 treated mice and macrophages in vitro may represent derepression of these target genes.

Figure 10A:
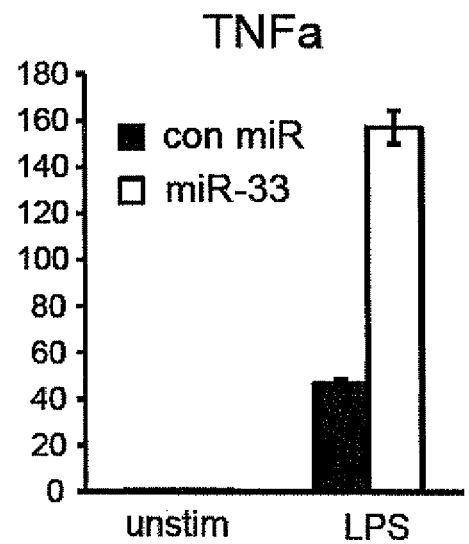
FIGS. 10A to 10E are bar graphs showing relative expression of TNFa (FIG. 10A), IL-1b (FIG. 10B), Arg1 (FIGS. 9C and 9D), IL-4 (FIG. 10E), Fizz1 (FIG. 9E), IL-10 (FIG. 9F) in peritoneal macrophages transfected with anti-miR-33 (open bars) or control anti-miR (solid bars bars) and stimulated with (right bars) and without (left bars) LPS.
Figure 10B:
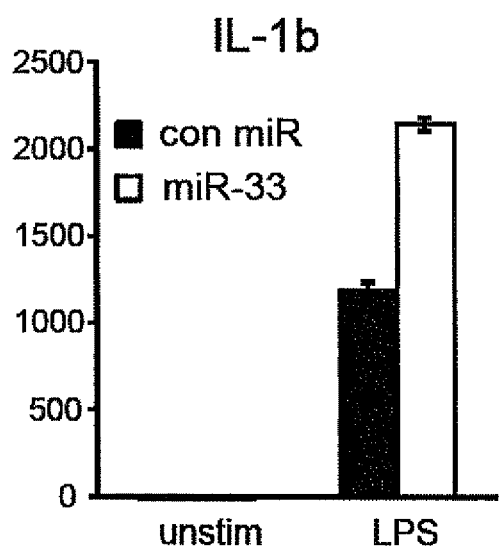
Figure 10C:
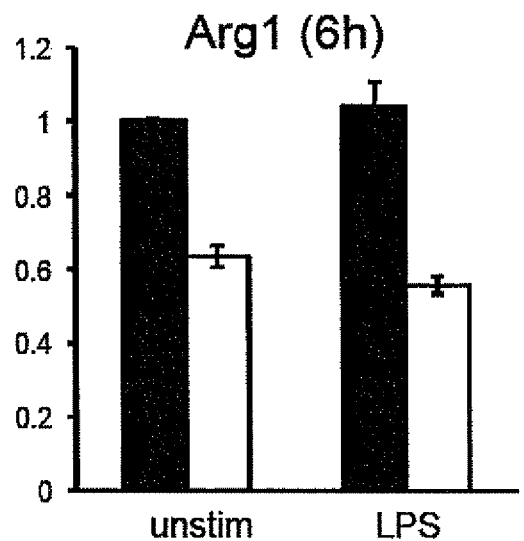
Figure 10D:
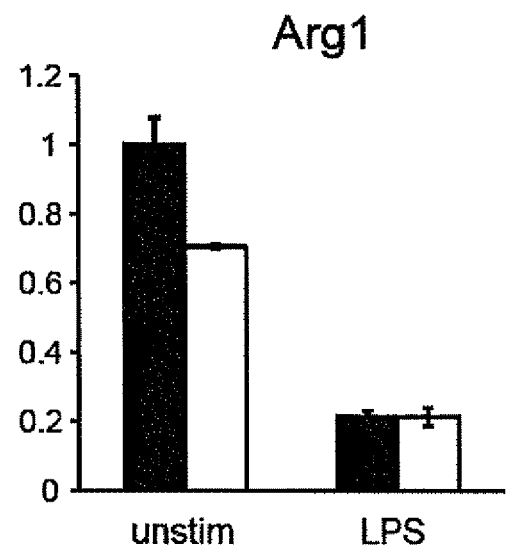
Figure 10E:
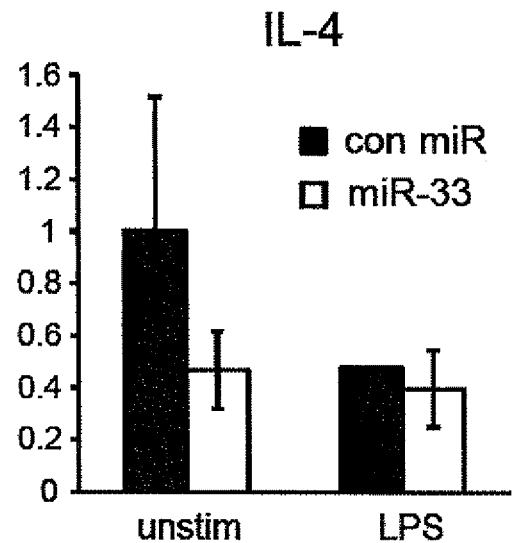
Figure 10F:
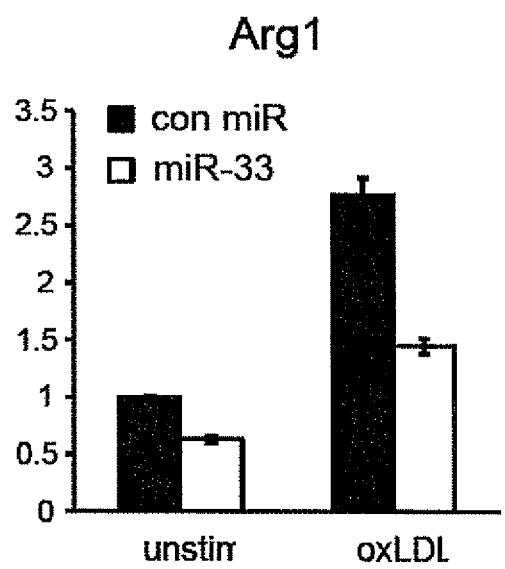
FIGS. 10F to 10G are bar graphs showing relative expression of Arg1 (FIG. 10F) and IL-4 (FIG. 100) in peritoneal macrophages transfected with anti-miR-33 (open bars) or control anti-miR (solid bars bars) and stimulated with (right bars) and without (left bars) oxidized LPS.
Figure 10G:
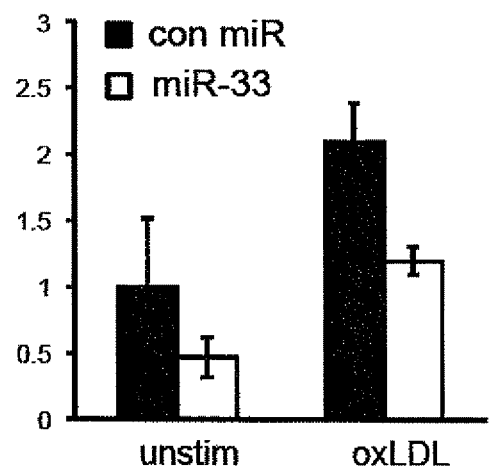

These findings were extended in an experiment in which peritoneal macrophages were transfected with a miR-33 mimic or control oligo and stimulated with and without LPS. Overexpression of miR-33 resulted in an increase in pro-inflammatory genes (TNFα, IL-1β; FIGS. 10A-10B) and a decrease in anti-inflammatory "M2" genes (Arg1 and IL-4; FIGS. 10D-10E). A similar decrease in M2 genes was seen in peritoneal macrophages transfected with miR-33 and stimulated with oxidized LDL, a proatherogenic lipid (FIGS. 10E-10G).

Figure 11A:
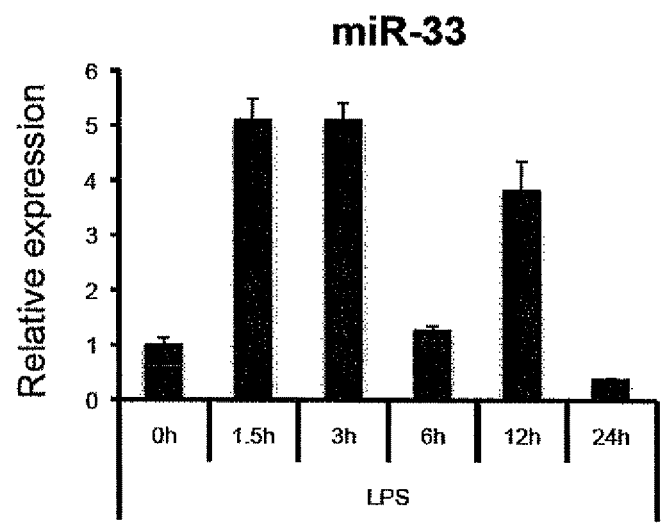
FIGS. 11A to 11C are bar graphs showing relative expression of miR-33 (FIG. 11A), pre-miR-33 (FIG. 11B), and SREBP2 mRNA in peritoneal macrophages stimulated with LPS for 0, 1.5, 3, 6, 12, and 24 hours.
Figure 11B:
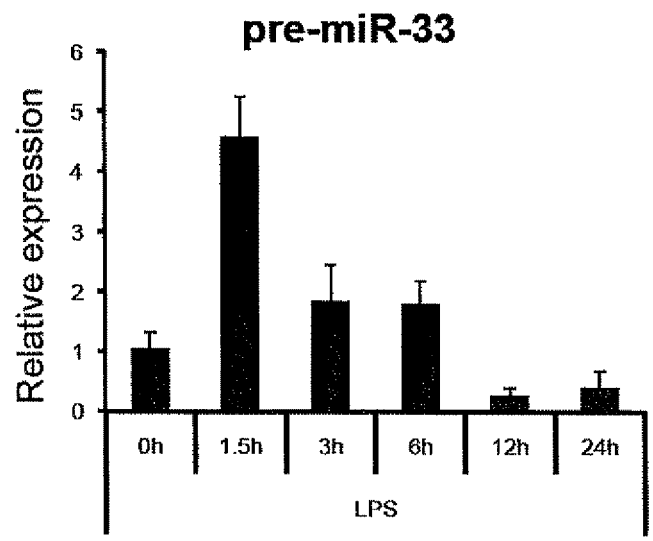
Figure 11C:
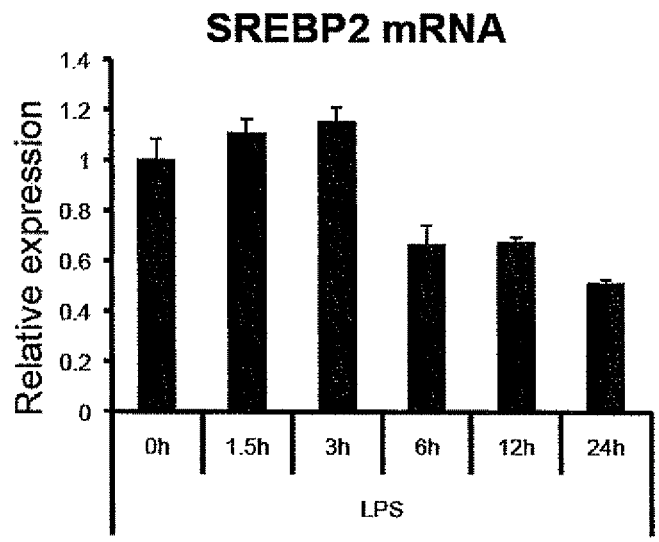

Notably, bacterial lipopolysaccharide (LPS) induces miR-33 expression but not expression of its host gene SREBP2, indicating that LPS, and potentially other inflammatory stimuli, may independently regulate miR-33 expression (FIGS. 11A-11C). Together these data point to a pro-inflammatory role for miR-33, and indicate that anti-miR-33 may be useful in reducing inflammation and promoting resolution of inflammation.

We claim:

1. A method for reducing inflammation comprising administering to a subject with an inflamed tissue comprising M1 macrophages, an inhibitor that specifically targets miR-33 in an amount effective to reduce inflammation in the tissue of the subject.

2. A method of reducing the progression of an inflammatory disease characterized by M1 macrophages in a subject comprising administering to the subject an effective amount of an inhibitor that specifically targets miR-33 to promote the polarization of the M1 macrophages in the subject from an M1 phenotype to an M2 phenotype.

3. The method of claim 2, wherein the subject has chronic inflammation.

4. The method of claim 2, wherein the subject has an autoimmune disease or disorder.

5. The method of claim 2, wherein the inflammatory disease is selected from the group consisting of acne vulgaris, asthma, atherosclerosis, autoimmune diseases, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, and interstitial cystitis.

6. The method of claim 1, wherein the miR-33 inhibitor is an antagomir.

7. The method of claim 6, wherein the antagomir is an antisense oligonucleotide comprising a single stranded nucleic acid sequence that is complementary to at least 12 contiguous nucleotides in miR-33, wherein the antisense oligonucleotide forms a duplex with miR-33 under physiological conditions.

8. The method of claim 7, wherein the single stranded nucleic acid sequence hybridizes under stringent conditions to an oligonucleotide consisting of the nucleic acid sequence SEQ ID NO:1, SEQ ID NO:2, SEQ ID NO:3, or SEQ ID NO:4.

9. The method of any one of claim 8, wherein the antisense oligonucleotide comprises one or more nucleotide modifications that increase stability of the antisense oligonucleotide in the presence of a nuclease.

10. The method of claim 9, wherein one or more of the nucleotide units of the antisense oligonucleotide are locked nucleic acid (LNA) units.

11. The method of claim 9, wherein one or more of the nucleotide units of the antisense oligonucleotide are 2' substituted nucleotide analogues.

12. The method of claim 11, wherein one or more of the internucleoside linkages between the nucleotide units of the antisense oligonucleotide are phosphorothioate internucleoside linkages.

13. The method of claim 1, wherein the inflamed tissue is cardiovascular tissue.

14. The method of claim 13, wherein the subject does not have established atherosclerotic plaques.

15. The method of the claim 2, wherein the subject has atherosclerotic inflammation, but does not have established atherosclerotic plaques.

16. The method of claim 15, wherein the miR-33 inhibitor is administered to the subject in an amount effective to reduce, delay, or slow the formation of new atherosclerotic plaques.

17. A method of reducing or preventing formation of atherosclerotic plaques comprising administering to a subject in need thereof, an inhibitor that specifically targets miR-33 in an amount effective to reduce inflammation in the vasculature of the subject.

18. The method claim 17, wherein the subject does not have established atherosclerotic plaques.

* * * * *